US00RE34960E

United States Patent [19]

Miyadera et al.

[11] E Patent Number: Re. 34,960

[45] Reissued Date of Patent: May 30, 1995

[54] CARBAPENEM COMPOUNDS, AND COMPOSITIONS CONTAINING THEM

[75] Inventors: Tetsuo Miyadera, Yokohama; Yukio Sugimura, Tokyo; Toshihiko Hashimoto, Toda; Teruo Tanaka, Yokohama; Kimio Iino; Tomoyuki Shibata, both of Tokyo, all of Japan; Shinichi Sugawara, New York, N.Y.

[73] Assignee: Sankyo Company, Limited, Tokyo, Japan

[21] Appl. No.: 52,849

[22] Filed: May 20, 1987

Related U.S. Patent Documents

Reissue of:

[64] Patent No.: 4,552,873
Issued: Nov. 12, 1985
Appl. No.: 407,914
Filed: Aug. 13, 1982

[30] Foreign Application Priority Data

Aug. 19, 1981 [JP] Japan ..... 56-129648
May 14, 1982 [JP] Japan ..... 57-81067

[51] Int. Cl.[6] ..... C07D 487/06; A61K 31/40
[52] U.S. Cl. ..... 514/210; 540/350
[58] Field of Search ..... 540/350; 514/210

[56] References Cited

U.S. PATENT DOCUMENTS 4,189,493 8/1980 Christensen et al. ..... 260/245.5 T
4,347,183 8/1982 Afonso et al. ..... 424/270
4,377,591 3/1983 Hiraoka et al. ..... 260/245.2 T
4,552,873 11/1985 Miyadera et al. ..... 540/350

FOREIGN PATENT DOCUMENTS 0001627 5/1979 European Pat. Off. .
0017992 10/1980 European Pat. Off. .
0024832 3/1981 European Pat. Off. .
0038869 11/1981 European Pat. Off. .
0040408 11/1981 European Pat. Off. .
0156281 12/1981 Japan .

*Primary Examiner*—Nicholas S. Rizzo
*Attorney, Agent, or Firm*—Frishauf, Holtz, Goodman & Woodward

[57] ABSTRACT

Compounds of formula (I):

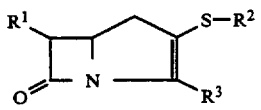

(I)

[[] wherein:

$R^1$ [represents a hydrogen atom, an alkyl group, an alkoxy group or various substituted alkyl groups] *is hydroxyethyl;*

$R^2$ represents a group of formula

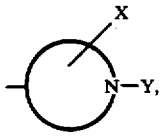

in which

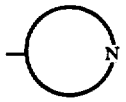

[represents an alicyclic amine group having from 4 to 8 ring atoms, optionally having a single double bond, optionally containing an additional hetero-atom and optionally having an oxo group on the ring;] *is a 3-pyrrolidinyl group;*

X represents a hydrogen atom[; an alkyl group, an alkoxy group, an alkylthio group, an alkylsulphinyl group, an alkylsulphonyl group, a hydroxy group, a halogen atom or various substituted alkyl groups];

Y represents [a hydrogen atom, an alkyl group, an aliphatic acyl group or an acylimidoyl] *an acetylimidoyl* group; and $R^3$ represents a carboxy group or a protected carboxy group[]]

and pharmaceutically acceptable salts thereof have valuable antibacterial activity, especially in vivo.

12 Claims, No Drawings

CARBAPENEM COMPOUNDS, AND COMPOSITIONS CONTAINING THEM

Matter enclosed in heavy brackets [ ] appears in the original patent but forms no part of this reissue specification; matter printed in italics indicates the additions made by reissue.

BACKGROUND OF THE INVENTION

The present invention relates to a series of new carbapenem compounds, to a process for preparing these compounds and to compositions containing the compounds.

The penicillins form a well-known class of antibiotics, which have found considerable use in human and animal therapy for many years. Chemically, the penicillins have in common a $\beta$-lactam structure, commonly referred to as "penam", which may be represented by the following formula:

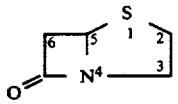

However, although the penicillins still form a valuable weapon in the pharmaceutical armory, the development of new, and often penicillin-resistant, strains of pathogenic bacteria has increasingly made it necessary to search for new types of antibiotic.

Recently, some interest has been shown in compounds having a carbapenem structure, that is compounds having a carbon atom in place of the sulphur atom at the 1-position and having a double bond between the carbon atoms in the 2- and 3-positions of the basic penam structure. The carbapenem structure may be represented by the following formula:

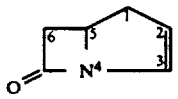

These penam and carbapenem structures form the basis for the semi-systematic nomenclature of the penicillin derivatives and this nomenclature is generally accepted by those skilled in the art throughout the world and is used herein. The numbering system employed herein is that illustrated on the above formulae.

Of the known carbapenem derivatives, the best known is a compound called "thienamycin", which may be represented by the following formula:

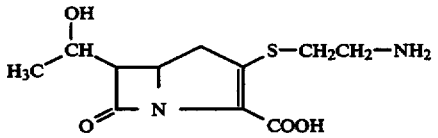

Although thienamycin is known to have remarkably potent and broad antibacterial activity, its chemical stability in the human body is poor, which restricts its practical use. Various attempts have, therefore, been made to modify the chemical structure of thienamycin in order to improve its chemical stability whilst maintaining its superior activity.

One class of compound which has been prepared in an attempt to overcome the stability problem of thienamycin has a heterocyclylthio group at the 2-position and compounds of this type are described in European Patent Specifications No. 1627 and No. 17992, whilst processes for preparing compounds of this type are described in European Patent Specifications No. 38869 and No. 40408 and in Japanese Patent Specification Kokai (i.e. published but unexamined) No. 156281/81.

We have now discovered a limited class of compounds which, whilst structurally similar to those disclosed in European Patent Specification No. 17992, have much improved antibacterial activity, especially in vivo activity, compared with the compounds disclosed in European Patent Specification No. 17922.

BRIEF SUMMARY OF INVENTION

The novel carbapenem derivatives of the present invention are those compounds of formula (I):

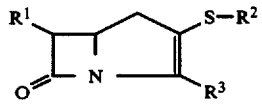

(I)

in which:

$R^1$ represents a hydrogen atom, an alkyl group, an alkoxy group or a group of formula $R^4A$- (in which $R^4$ represents a hydroxy group, a protected hydroxy group, an alkoxy group, a mercapto group, a protected mercapto group, an amino group or a protected amino group, and A represents a bivalent acyclic saturated hydrocarbon group which is unsubstituted or has a substituent selected from trifluoromethyl and phenyl groups);

$R^2$ represents a group of formula

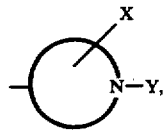

in which

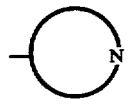

represents an alicyclic amine group having from 4 to 8 ring atoms (including the nitrogen atom shown) and optionally having a single double bond, which amine group may optionally contain at least one additional heteroatom selected from nitrogen, oxygen and sulphur atoms, and which may optionally have an oxo group on the heterocyclic ring;

X represents a hydrogen atom, an alkyl group, a cyanoalkyl group, a haloalkyl group, an alkoxyalkyl group, an alkylthioalkyl group, an alkoxycarbonylalkyl group, an alkoxy group, an alkylthio group, an alkylsulphinyl group, an alkylsulphonyl group, a hydroxy group or a halogen atom;

Y represents a hydrogen atom, or an alkyl or aliphatic acyl group optionally having a substituent selected from hydroxy, amino, alkoxy and carboxy groups, or a group of formula

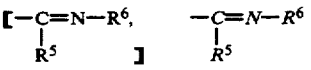

in which $R^5$ and $R^6$ are the same or different and each represents a hydrogen atom or an alkyl group; and $R^3$ represents a carboxy group or a protected carboxy group; and pharmaceutically acceptable salts thereof.

The invention also provides a pharmaceutical composition comprising an effective amount of an antibacterial agent in admixture with a pharmaceutically acceptable carrier or diluent, wherein the antibacterial agent is at least one compound of formula (I) or salt thereof.

The invention still further provides a method of treating bacterial infections by the administration of an antibacterial agent, wherein the antibacterial agent is at least one compound of formula (I) or salt thereof.

The invention still further provides a process for preparing the compounds of formula (I) and salts thereof, which process comprises either reacting a compound of formula (II):

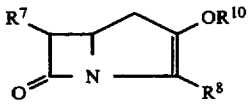

(II)

(in which $R^7$ represents any one of the groups defined for $R^1$, in which any hydroxy, mercapto or amino group is optionally protected, $R^8$ represents a protected carboxy group, and $R^{10}$ represents an alkylsulphonyl group, an arylsulphonyl group, a dialkylphosphoryl group or a diarylphosphoryl group) with a mercaptan of formula (III):

$$HS\text{-}R^{11} \qquad \text{(III)}$$

(in which $R^{11}$ represents a group of formula

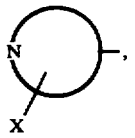

in which

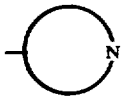

is as defined above, whose nitrogen atom is protected) to give a compound of formula (IV):

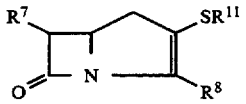

(IV)

(in which $R^7$, $R^8$ and $R^{11}$ are as defined above) and, if necessary, removing a protecting group or groups from the compound of formula (IV) to give a compound of formula (I) in which Y represents a hydrogen atom and, if necessary, converting the hydrogen atom represented by Y in said compound of formula (I) to one of the other groups represented by Y in said compound; or where Y represents an alkyl or an aliphatic acyl group optionally having a substituent selected from hydroxy, amino. alkoxy and carboxy groups or a group of formula

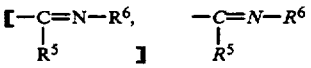

reacting said compound of formula (II) with a compound of formula (V):

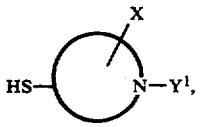

(V)

(in which X and

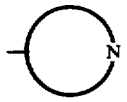

are as defined above and Y′ represents an alkyl group, an aliphatic acyl group or a group of formula

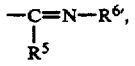

in which $R^5$ is as defined above and $R^{6'}$ represents any one of the groups defined for $R^6$ or a protecting group for the nitrogen atom) and, if necessary, removing any protecting groups from the resulting compound.

DETAILED DESCRIPTION OF INVENTION

In the compounds of formula (I), when $R^1$ represents an alkyl group, it may be a straight or branched chain group and is preferably a group having from 1 to 6 carbon atoms, for example a methyl, ethyl, propyl, isopropyl, butyl, isobutyl, sec-butyl, t-butyl, pentyl, isopentyl or hexyl group.

When $R^1$ represents an alkoxy group, it may be a straight or branched chain group and is preferably a group having from 1 to 4 carbon atoms, i.e. a methoxy, ethoxy, propoxy, isopropoxy, butoxy, isobutoxy, sec-butoxy or t-butoxy group.

When $R^1$ represents a group of formula $R^4A$- and $R^4$ represents an alkoxy group, this alkoxy group may be a straight or branched chain group and is preferably a group having from 1 to 3 carbon atoms, i.e. a methoxy, ethoxy, propoxy or isopropoxy group.

When $R^4$ represents a protected hyroxy group, this is preferably an acyloxy group, an alkylsulphonyloxy group, an arylsulphonyloxy group or a trialkylsilyloxy group. Where $R^4$ represents a protected mercapto group, this is preferably an alkylthio group, and, where $R^4$ represents a protected amino group, this is preferably an acylamino group.

Preferred acyloxy groups which may be represented by $R^4$ are aliphatic acyloxy groups having from 1 to 5 carbon atoms, for example the formyloxy, acetoxy, propionyloxy, butyryloxy, isobutyryloxy, sec-butyryloxy, t-butyryloxy, valeryloxy or isovaleryloxy groups, or the aralkyloxycarbonyloxy groups, particularly a benzyloxycarbonyloxy group which may be unsubstituted or may have a nitro or methoxy substituent in its phenyl moiety (for example, the benzyloxycarbonyloxy, o-nitrobenzyloxycarbonyloxy, p-nitrobenzyloxycarbonyloxy or p-methoxybenzyloxycarbonyloxy groups).

Preferred alkylsulphonyloxy groups which may be represented by $R^4$ are such groups having from 1 to 3 carbon atoms, for example the methanesulphonyloxy, ethanesulphonyloxy and propanesulphonyloxy groups.

Preferred arylsulphonyloxy groups which may be represented by $R^4$ are the benzenesulphonyloxy group, which may be unsubstituted or may have a methyl substituent, particularly the benzenesulphonyloxy and p-toluenesulphonyloxy groups.

Preferred trialkylsilyloxy groups which may be represented by $R^4$ are those in which each alkyl moiety has from 1 to 4 carbon atoms, for example the trimethylsilyloxy and t-butyldimethylsilyloxy groups.

Preferred alkylthio groups which may be represented by $R^4$ are groups having from 1 to 5 carbon atoms, for example the methylthio, ethylthio, propylthio, isopropylthio, butylthio, isobutylthio, sec-butylthio, t-butylthio, pentylthio and isopentylthio groups.

Preferred acylamino groups which may be represented by $R^4$ are the aliphatic acylamino groups having from 1 to 5 carbon atoms, for example the formylamino, acetylamino, propionylamino, butyrylamino, isobutyrylamino and valerylamino groups.

When $R^1$ represents a group of formula $R^4A$-, A represents a saturated acyclic hydrocarbon group, which may be a straight or branched chain group, optionally having a trifluoromethyl or phenyl substituent. The hydrocarbon group represented by A preferably has from 1 to 5 carbon atoms. Examples of such groups include the methylene, ethylene, ethylidene, trimethylene, propylidene, isopropylidene, tetramethylene, butylidene, pentamethylene, pentylidene, 2,2,2-trifluoroethylidene, 3,3,3-trifluoropropylidene and benzylidene groups.

The group of formula

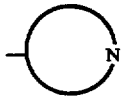

preferably represents a 2-azetidinyl, 3-azetidinyl, 2-pyrrolidinyl, 3-pyrrolidinyl, 2-piperidyl, 3-piperidyl, 4-piperidyl, 2-morpholinyl, 3-morpholinyl, 2-thiazolidinyl, 4-thiazolidinyl, 5-thiazolidinyl, 2,3,5,6-tetrahydro-4H-thiazin-2-yl, 2,3,5,6-tetrahydro-4H-thiazin-3-yl or 3,4,5,6-tetrahydropyrimidin-5-yl group.

When X represents an alkyl group, a cyanoalkyl group, a haloalkyl group, an alkoxyalkyl group, an alkylthioalkyl group, an alkoxycarbonylalkyl group, an alkoxy group, an alkylthio group, an alkylsulphinyl group or an alkylsulphonyl group, each alkyl, alkoxy or alkylthio moiety preferably has from 1 to 4 carbon atoms, for example the methyl, ethyl, propyl, isopropyl, butyl, isobutyl, sec-butyl or t-butyl groups or analogues thereof.

When X represents a halogen atom, it is preferably a fluorine, chlorine, bromine or iodine atom.

When Y represents an alkyl group optionally having an amino, hydroxy, alkoxy or carboxy substituent, the alkyl group preferably has from 1 to 4 carbon atoms. Examples of such groups include the methyl, ethyl, propyl, isopropyl, butyl, isobutyl, aminomethyl, hydroxymethyl, carboxymethyl, methoxymethyl, 2-aminoethyl, 2-hydroxyethyl, 2-carboxyethyl, 2-aminopropyl, 3-aminopropyl, 4-aminopropyl and 2-amino-1-methylethyl groups.

When Y represents an aliphatic acyl group optionally having an amino, hydroxy, alkoxy or carboxy substituent, the acyl group itself preferably has from 1 to 5 carbon atoms and may be, for example, a formyl, acetyl, propionyl, butyryl or isobutyryl group. If the acyl group has one of the above-mentioned substituents, it is preferably a group derived from an amino acid (such as glycine, alanine, serine, threonine or aspartic acid), from an oxy-acid (such as glycolic acid) or from a dibasic acid (such as succinic acid or fumaric acid).

Where Y represents a group of formula $$[-\underset{\underset{R^5}{|}}{C}=N-R^6, \qquad -\underset{\underset{R^5}{|}}{C}=N-R^6]$$

and where $R^5$ and/or $R^6$ represents an alkyl group, the alkyl group preferably has from 1 to 4 carbon atoms, for example a methyl, ethyl, propyl, isopropyl, butyl or isobutyl group.

When $R^3$ represents a protected carboxyl group, it is preferably a group of formula —$COOR^{3'}$, where $R^{3'}$ is a carboxy-protecting group. This carboxy-protecting group represented by $R^{3'}$ is preferably: an alkyl group having from 1 to 4 carbon atoms, for example a methyl, ethyl, propyl, isopropyl, butyl, isobutyl or t-butyl group; a haloalkyl group having 1 or 2 carbon atoms, for example a 2-iodoethyl, 2,2-dibromoethyl or 2,2,2-trichloroethyl group; an alkoxymethyl group having from 1 to 4 carbon atoms in the alkoxy moiety, for example a methoxymethyl, ethoxymethyl, propoxymethyl, isopropoxymethyl, butoxymethyl, isobutoxymethyl or t-butoxymethyl group; an aliphatic acyloxymethyl group having from 1 to 6 carbon atoms in the acyloxy moiety, for example a formyloxymethyl, acetoxymethyl, propionyloxymethyl, butyryloxymethyl, isobutyryloxymethyl, pivaloyloxymethyl, valeryloxymethyl or t-pentanoyloxymethyl group; a 1-alkoxycarbonyloxyethyl group having from 1 to 5 carbon atoms in its alkoxy moiety, for example a 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-pentyloxycarbonyloxyethyl or 1-(1-ethylpropoxy)carbonyloxyethyl group; an aralkyl group, particularly a benzyl group which may be unsubstituted or have a nitro or methoxy substituent in its phenyl moiety, for example a benzyl, p-methoxybenzyl, o-nitrobenzyl or p-nitrobenzyl group; a benzhydryl group; a phthalidyl group; an alkenyl group having from 3 to 5 carbon atoms, for example an alkyl, methallyl or butenyl group; or a (5-methyl-1,3-dioxolen-2-one-4-yl)methyl group.

We particularly prefer those compounds of formula (I) in which $R^1$ represents a hydrogen atom, an alkyl group having 2 or 3 carbon atoms, a 1-hydroxyethyl group, a 1-(aliphatic acyloxy)ethyl group having from 1 to 5 carbon atoms in its acyl moiety or a 1-hydroxy-1-methylethyl group, most preferably a 1-hydroxyethyl group.

The group represented by the formula

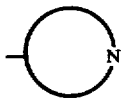

is more preferably a 2-azetidinyl, 3-azetidinyl, 2-pyrrolidinyl, 3-pyrrolidinyl, 2-piperidyl, 3-piperidyl, 4-piperidyl, 2-morpholinyl, 3-morpholinyl, 2-thiazolidinyl, 4-thiazolidinyl, 5-thiazolidinyl, 2,3,5,6-tetrahydro-4H-thiazin-2-yl, 2,3,5,6-tetrahydro-4H-thiazin-3-yl or 3,4,5,6-tetrahydropyrimidin-5-yl group, more preferably a 3-pyrrolidinyl or 3,4,5,6-tetrahydropyrimidin-5-yl group, most preferably a 3-pyrrolidinyl group.

The group represented by X is preferably a hydrogen atom, an alkyl group having from 1 to 4 carbon atoms, an alkoxyalkyl group having from 1 to 4 carbon atoms in each of its alkoxy and its alkyl moieties, a cyanoalkyl group having from 1 to 4 carbon atoms in its alkyl moiety, an alkylthioalkyl group having from 1 to 4 carbon atoms in each of its alkyl moieties, a haloalkyl group having from 1 to 4 carbon atoms, an alkoxycarbonylalkyl group having from 1 to 4 carbon atoms in each of its alkoxy and its alkyl moieties, an alkoxy, alkylthio, alkylsulphinyl or alkylsulphonyl group, each having from 1 to 4 carbon atoms, a hydroxy group or a halogen atom. More preferred atoms and groups represented by X are a hydrogen atom or the aforementioned alkoxyalkyl, cyanoalkyl, alkoxy, alkylthio and alkylsulphinyl groups, most preferably a hydrogen atom or a methyl, ethyl or methoxymethyl group, especially a hydrogen atom.

The group represented by Y is preferably a hydrogen atom, an alkyl group having from 1 to 4 carbon atoms, an aliphatic acyl group having from 1 to 5 carbon atoms or a group of formula $$[-\underset{\underset{R^5}{|}}{C}=N-R^6, \quad -\underset{\underset{R^5}{|}}{C}=N-R^6]$$

in which $R^5$ and $R^6$ are the same or different and each represents a hydrogen atom or an alkyl group having from 1 to 4 carbon atoms. The group represented by Y is more preferably a hydrogen atom, a group of formula $$-\underset{\underset{R^5}{|}}{C}=N-R^6$$

(in which $R^5$ and $R^6$ are as defined) or an aliphatic acyl group having from 1 to 5 carbon atoms, most preferably a group of formula $$[-\underset{\underset{R^5}{|}}{C}=N-R^6, \quad -\underset{\underset{R^5}{|}}{C}=N-R^6]$$

especially an acetimidoyl group.

The group represented by $R^3$ is preferably a carboxyl group.

The compounds of the present invention may exist in the form of various optical isomers, because of the presence of various asymmetric carbon atoms, and may also exist in the form of various geometric isomers. All of the isomers are represented by a single, plane formula in the specification and claims; however, the present invention contemplates the use of either the individual isomers or of mixtures, e.g. racemates, thereof. However, preferred compounds are those having the same configuration as does thienamycin, that is to say the (5R, 6S) configuration. If the group represented by $R^1$ in the compounds of formula (I) has a further substituent at its $\alpha$-position, for example a hydroxy or acetoxy group at the $\alpha$-position of an ethyl group, then the preferred configuration of this further substituent is the R-configuration.

In those compounds of formula (I) where Y represents a group of formula $$[-\underset{\underset{R^5}{|}}{C}=N-R^6, \quad -\underset{\underset{R^5}{|}}{C}=N-R^6]$$

then there may be some double bond character to the bond between the nitrogen atom of the group of formula

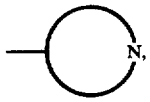

and the carbon atom adjacent thereto of the group of formula $$-\underset{\underset{R^5}{|}}{C}=N-R^6.$$

This will form syn- and anti-isomers, which are normally readily interconvertible, as shown in the following formulae:

Both of these isomers are contemplated by the present invention.

Compounds of formula (I) in which $R^3$ represents a carboxy group may be readily converted to pharmaceutically acceptable salts by conventional means. Examples of such salts include metal salts (for example the lithium, sodium, potassium, calcium and magnesium salts), salts with ammonia and organic amines (for example the ammonium, cyclohexylammonium, diisopropylammonium and triethylammonium salts) and salts with other basic compounds, including basic amino-acids (for example the arginine and lysine salts).

Because of the presence of a basic nitrogen atom in the group of formula

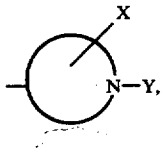

compounds of formula (I) in which $R^3$ represents a protected carboxy group (for example a pivaloyloxymethoxycarbonyl group) will also form acid addition salts and those salts which are pharmaceutically acceptable also form part of the present invention. Examples of acids which will form such salts include inorganic acids (for example hydrochloric, hydrobromic, sulphuric and phosphoric acids) and organic acids (for example formic, acetic, methanesulphonic, p-toluenesulphonic and glutamic acids).

The compounds may also form adducts with water or with organic solvents and these, also, form part of the present invention.

Examples of compounds of the invention are given in the following list; the compounds are hereinafter identified by the numbers assigned to them in this list.

1. 2-(Azetidin-3-ylthio)-6-(1-hydroxyethyl)-2-carbapenem-3-carboxylic acid
2. 6-(1-Hydroxyethyl)-2-(pyrrolidin-3-ylthio)-2-carbapenem-3-carboxylic acid
3. 6-(1-Hydroxyethyl)-2-(piperidin-3-ylthio)-2-carbapenem-3-carboxylic acid
4. 6-(1-Hydroxyethyl)-2-(piperidin-4-ylthio)-2-carbapenem-3-carboxylic acid
5. 2-(1-Formimidoylazetidin-3-ylthio)-6-(1-hydroxyethyl)-2-carbapenem-3-carboxylic acid
6. 2-(1-Formimidoylpyrrolidin-3-ylthio)-6-(1-hydroxyethyl)-2-carbapenem-3-carboxylic acid
7. 2-(1-Formimidoylpiperidin-4-ylthio)-6-(1-hydroxyethyl)-2-carbapenem-3-carboxylic acid
8. 2-(1-Acetimidoylazetidin-3-ylthio)-6-(1-hydroxyethyl)-2-carbapenem-3-carboxylic acid
9. 2-(1-Acetimidoylpyrrolidin-3-ylthio)-6-(1-hydroxyethyl)-2-carbapenem-3-carboxylic acid
10. 2-(1-Acetimidoylpiperidin-3-ylthio)-6-(1-hydroxyethyl)-2-carbapenem-3-carboxylic acid
11. 2-(Pyrrolidin-3-ylthio)-2-carbapenem-3-carboxylic acid
12. 6-Ethyl-2-(pyrrolidin-3-ylthio)-2-carbapenem-3-carboxylic acid
13. 6-(1-Hydroxy-1-methylethyl)-2-(pyrrolidin-3-ylthio)-2-carbapenem-3-carboxylic acid
14. 2-(1-Formimidoylpyrrolidin-3-ylthio)-6-(1-hydroxy-1-methylethyl)-2-carbapenem-3-carboxylic acid
15. p-Nitrobenzyl 6-(1-hydroxyethyl)-2-(1-p-nitrobenzyloxycarbonylpyrrolidin-3-ylthio)-2-carbapenem-3-carboxylate
16. Pivaloyloxymethyl 6-(1-hydroxyethyl)-2-(pyrrolidin-3-ylthio)-2-carbapenem-3-carboxylate hydrochloride
17. Pivaloyloxymethyl 2-(azetidin-3-ylthio)-6-(1-hydroxyethyl)-2-carbapenem-3-carboxylate hydrochloride
18. Pivaloyloxymethyl 6-(1-hydroxyethyl)-2-(piperidin-4-ylthio)-2-carbapenem-3-carboxylate hydrochloride
19. 2-(1-Acetimidoyl-4-methylthiopyrrolidin-3-ylthio)-6-(1-hydroxyethyl)-2-carbapenem-3-carboxylic acid
20. 2-(1-Acetimidoyl-4-methylsulphinylpyrrolidin-3-ylthio)-6-(1-hydroxyethyl)-2-carbapenem-3-carboxylic acid
21. 2-(1-Acetimidoyl-4-methylsulphonylpyrrolidin-3-ylthio)-6-(1-hydroxyethyl)-2-carbapenem-3-carboxylic acid
22. 2-(1-Acetimidoyl-4-methylpyrrolidin-3-ylthio)-6-(1-hydroxyethyl)-2-carbapenem-3-carboxylic acid
23. 2-(1-Acetimidoyl-4-hydroxypyrrolidin-3-ylthio)-6-(1-hydroxyethyl)-2-carbapenem-3-carboxylic acid
24. 2-(1-Acetimidoyl-4-fluoropyrrolidin-3-ylthio)-6-(1-hydroxyethyl)-2-carbapenem-3-carboxylic acid
25. 2-(1-Acetimidoylpyrrolidin-3-ylthio)-6-(1-acetoxyethyl)-2-carbapenem-3-carboxylic acid
26. 2-(1-Acetimidoylpyrrolidin-3-ylthio)-6-(1-propionyloxyethyl)-2-carbapenem-3-carboxylic acid
27. 2-(1-Formylpyrrolidin-3-ylthio)-6-(1-hydroxyethyl)-2-carbapenem-3-carboxylic acid
28. 2-(1-Acetylpyrrolidin-3-ylthio)-6-(1-hydroxyethyl)-2-carbapenem-3-carboxylic acid
29. 6-(1-Hydroxyethyl)-2-(1-propionylpyrrolidin-3-ylthio)-2-carbapenem-3-carboxylic acid
30. 2-(1-Butyrylpyrrolidin-3-ylthio)-6-(1-hydroxyethyl)-2-carbapenem-3-carboxylic acid
31. 6-(1-Hydroxyethyl)-2-(1-methylpyrrolidin-3-ylthio)-2-carbapenem-3-carboxylic acid
32. 2-(1-Ethylpyrrolidin-3-ylthio)-6-(1-hydroxyethyl)-2-carbapenem-3-carboxylic acid
33. 6-(1-Hydroxyethyl)-2-(1-propylpyrrolidin-3-ylthio)-2-carbapenem-3-carboxylic acid
34. 2-(1-Butylpyrrolidin-3-ylthio)-6-(1-hydroxyethyl)-2-carbapenem-3-carboxylic acid
35. 6-(1-Hydroxyethyl)-2-(1-isobutylpyrrolidin-3-ylthio)-2-carbapenem-3-carboxylic acid
36. 6-(1-Hydroxyethyl)-2-(2-methoxymethyl-3,4,5,6-tetrahydropyrimidin-5-ylthio)-2-carbapenem-3-carboxylic acid
37. 2-(2-Ethyl-3,4,5,6-tetrahydropyrimidin-5-ylthio)-6-(1-hydroxyethyl)-2-carbapenem-3-carboxylic acid
38. 6-(1-Hydroxyethyl)-2-(2-isopropyl-3,4,5,6-tetrahydropyrimidin-5-ylthio)-2-carbapenem-3-carboxylic acid
39. 6-(1-Hydroxyethyl)-2-(2-methyl-3,4,5,6-tetrahydropyrimidin-5-ylthio)-2-carbapenem-3-carboxylic acid
40. 2-(1-Glycylpyrrolidin-3-ylthio)-6-(1-hydroxyethyl)-2-carbapenem-3-carboxylic acid
41. 2-(1-Alanylpyrrolidin-3-ylthio)-6-(1-hydroxyethyl)-2-carbapenem-3-carboxylic acid
42. 2-(1-β-Alanylpyrrolidin-3-ylthio)-6-(1-hydroxyethyl)-2-carbapenem-3-carboxylic acid
43. 2-(1-α-Hydroxyacetylpyrrolidin-3-ylthio)-6-(1-hydroxyethyl)-2-carbapenem-3-carboxylic acid
44. 6-(1-Hydroxyethyl)-2-(1-β-hydroxypropionylpyrrolidin-3-ylthio)-2-carbapenem-3-carboxylic acid
45. 6-(1-Hydroxyethyl)-2-(1-α-methoxyacetylpyrrolidin-3-ylthio)-2-carbapenem-3-carboxylic acid
46. 2-(1-β-Carboxypropionylpyrrolidin-3-ylthio)-6-(1-hydroxyethyl)-2-carbapenem-3-carboxylic acid
47. (5R, 6S)-6-[1-(R)-Acetoxyethyl]-2-(pyrrolidin-3-ylthio)-2-carbapenem-3-carboxylic acid
48. (5R, 6S)-6-[1-(R)-Hydroxyethyl]-2-(4-methylthiopyrrolidin-3-ylthio)-2-carbapenem-3-carboxylic acid
49. (5R, 6S)-6-[1-(R)-Hydroxyethyl]-2-(4-methylsulphinylpyrrolidin-3-ylthio)-2-carbapenem-3-carbaxylic acid
50. (5R, 6S)-6-[1-(R)-Hydroxyethyl]-2-(4-methoxypyrrolidin-3-ylthio)-2-carbapenem-3-carboxylic acid 51. (5R, 6S)-6-[1-(R)-Hydroxyethyl]-2-(3,4,5,6-tetrahydropyrimidin-5-ylthio)-2-carbapenem-3-carboxylic acid 52. (5R, 6S)-2-(2-Cyanomethyl-3,4,5,6-tetrahydropyrimidin-5-ylthio)-6-[1-(R)-hydroxyethyl]-2-carbapenem-3-carboxylic acid Of the compounds listed above, the preferred compounds are Compounds No. 9, 2, 28, 36, 37 and 38, Compounds No. 9, 2, 28 and 36 being most preferred.

The compounds of the present invention can be prepared by the methods summarised in the following reaction scheme:

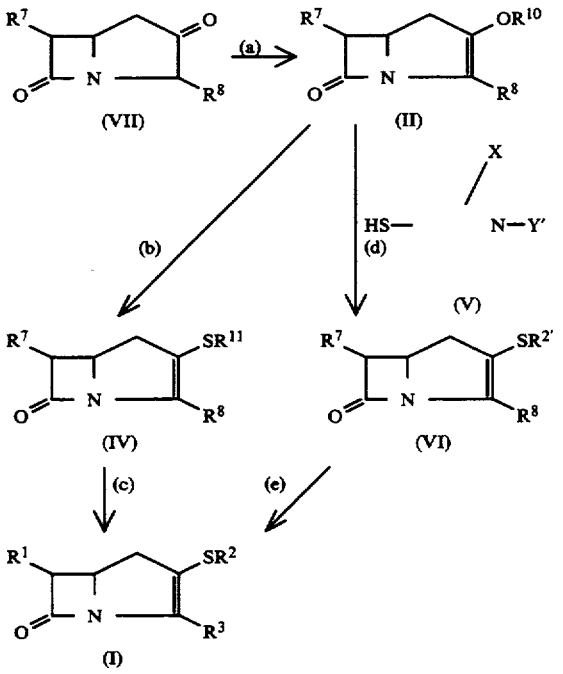

In the above formulae, $R^1$, $R^2$ and $R^3$ are as defined above. $R^7$ represents any of the groups represented by $R^1$ but in which any reactive groups have been protected, that is to say a hydrogen atom, an alkyl group, an alkoxy group or a group of formula $R^9A$-, in which $R^9$ represents an alkoxy group, a protected hydroxy group, a protected mercapto group or a protected amino group and A represents a bivalent saturated acylic hydrocarbon group optionally having a trifluoromethyl or phenyl substituent. $R^8$ represents a protected carboxy group. $R^{10}$ represents an alkylsulphonyl group, an arylsulphonyl group, a dialkylphosphoryl group or a diarylphosphoryl group. $R^{11}$ represents a group of formula

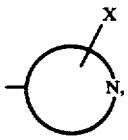

whose nitrogen atom is protected and in which, if desired, any reactive groups represented by or in the group represented by X are also protected. Y' represents an alkyl or, an aliphatic acyl group optionally having a substituent selected from hydroxy, amino, alkoxy and carboxy groups, or a group of formula

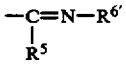

(in which $R^{6'}$ represents any of the groups defined for $R^6$, except that, where $R^6$ represents a hydrogen atom, $R^{6'}$ preferably represents a protecting group for the nitrogen atom). $R^{2'}$ represents the group represented by $R^2$, except that any reactive atom or group is protected.

One of the alternative process schemes illustrated in the above reaction scheme comprises:

Step a

Reacting a compound of formula (VII) with an alkanesulphonic acid anhydride, an arenesulphonic acid anhydride, a dialkylphosphoryl halide or a diarylphosphoryl halide in the presence of a base to produce the compound of formula (II);

Step b

Reacting the compound of formula (II), preferably without intermediate isolation, with a mercaptan of formula (III);

$$HS\text{-}R^{11} \qquad (III)$$

to produce a compound of formula (IV) and

Step c

If necessary, subjecting the compound of formula (IV) to any necessary reactions to remove protecting groups and, if necessary, converting the group of formula

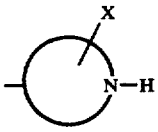

to a group of formula

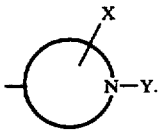

Steps (a) and (b) of this process are preferably both conducted in the presence of a base and in an inert solvent. The nature of the solvent employed is not critical, provided that it has no adverse effect on the reaction. Examples of suitable solvents include: halogenated hydrocarbons, such as methylene chloride, ethylene dichloride or chloroform; nitriles, such as acetonitrile; and amides, such as N,N-dimethylformamide or N,N-dimethylacetamide. There is also no particular limitation on the nature of the base employed in these reactions, provided that it does not affect other parts of the compound, especially the β-lactam ring; suitable bases for step (A) include such organic bases as triethylamine, diisopropylethylamine and 4-dimethylaminopyridine.

Examples of the reagent employed in step (a) include: alkanesulphonic acid anhydrides, preferably having from 1 to 5 carbon atoms, for example methanesulphonic acid anhydride or ethanesulphonic acid anhydride; arenesulphonic acid anhydrides, preferably benzenesulphonic acid anhydrides optionally having a methyl substituent, for example benzenesulphonic acid anhydride or p-toluenesulphonic acid anhydride; dialkylphosphoryl halides, preferably having from 1 to 5 carbon atoms in each alkyl moiety, for example dimethylphosphoryl chloride or diethylphosphoryl chloride; and diarylphosphoryl halides, preferably diphenylphosphoryl halides, for example diphenylphosphoryl chloride or diphenylphosphoryl bromide. Of these reagents, p-toluenesulphonic acid anhydride and diphenylphosphoryl chloride are particularly preferred.

The reaction temperature in step (a) is not particularly critical but, in order to control side reactions, we prefer to carry out the reaction at a relatively low temperature, for example from −20° C. to 40° C. The time required for the reaction will depend mainly upon the reaction temperature and the nature of the starting materials, but it is generally from 10 minutes to 5 hours.

The compound of formula (II) thus obtained is then, preferably without intermediate isolation, reacted with the mercaptan of formula (III) in the presence of a base. Suitable bases include such organic bases as triethylamine and diisopropylethylamine and such inorganic bases as potassium carbonate and sodium carbonate. Even where step (a) is effected in the presence of a base and where step (b) is carried out without isolation of the product of step (a), additional base is preferably added. There is no particular limitation on the reaction temperature, although, as with step (a), the reaction is preferably carried out at a relatively low temperature, e.g. from −20° C. to ambient temperature. The time required for the reaction may vary from 30 minutes to 8 hours.

After completion of the reaction, the desired compound of formula (IV) may be recovered from the reaaction mixture by conventional methods. For example, in one suitable procedure, a water-immiscible organic solvent is added to the reaction mixture or to a residue obtained by distilling the solvent from the reaction mixture. The resulting mixture is washed with water and then the solvent is distilled off, to give the desired product which may, if necessary, be further purified by conventional means, for example by recrystallisation, reprecipitation, chromatography or any combination thereof.

Finally, if necessary, the resulting compound of formula (IV) may be converted to the compound of formula (I) by removing protecting groups. The nature of the removal reaction depends upon the particular protecting group involved and, where there are two or more protecting groups in the compound of formula (IV), these may be removed sequentially or, by appropriate choice of protecing groups and reactions, two or more protecting groups may be removed together.

Thus, in the case of the group represented by $R^8$, which is a protected carboxy group, the protecting group may be removed by various methods. For example, if the carboxy-protecting group is a group removable by reduction (e.g. a halogenated alkyl group or an aralkyl group, including the benzhydryl group), the compound of formula (IV) is contacted with a reducing agent. Where the carboxy-protecting group is a halogenated alkyl group (e.g. a 2,2-dibromoethy group or a 2,2,2-trichloroethyl group), a preferred reducing agent is a combination of zinc with acetic acid. Where the protecting group is an aralkyl group (e.g. a benzyl group, a p-nitrobenzyl group or a benzhydryl grop), the reduction is preferably a catalytic reduction reaction using platinum or palladium on charcoal as the catalyst or employs an alkali metal sulphide (such as sodium sulphide or potassium sulphide) as the reducing agent. These reactions are normally carried out in the presence of a solvent, the nature of which is not critical, provided that it has no adverse effect on the reaction. Preferred solvents include alcohols (such as methanol or ethanol), ethers (such as tetrahydrofuran or dioxane) and mixtures of one or more of these organic solvents with water. There is no particular limitation on the reaction temperature, although it is usually from 0° C. to about ambient temperature. The time required for the reaction will depend upon the nature of the starting materials and the reducing agents, but the reaction will usually be complete within from 5 minutes to 12 hours.

After completion of the reaction, the resulting compound may be recovered from the reaction mixture by conventional means: for example, the insolubles are filtered off, the resulting solution is washed with water and dried, and then the solvent is distilled off to give the desired product. This product may, if necessary, be further purified by conventional means, for example by recrystallisation, preparative thin layer chromatography or column chromatography.

When the group represented by $R^7$ in the compound of formula (IV) is an acyloxy group, a trialkylsilyloxy group, an acylamino group or an aralkylamino group or when the nitrogen atom contained in the group represented by $R^{11}$ has a protecting group (such as an acyl group or an aralkyloxycarbonyl group), the protecting groups may, if so required, be removed by conventional means, e.g. as illustrated below, to restore a hydroxy group or an amino group. Removal of these protecting groups may be carried out before, simultaneously with or after removal of the carboxy-protecting group included in the group represented by $R^8$ and this reaction is preferably carried out before or at the same time as removal of the carboxy-protecting group.

When the group represented by $R^7$ contains a lower aliphatic acyloxy group (for example an acetoxy group), this group may be removed and the desired hydroxy group restored by treating the compound of formula (IV) with a base in the presence of an aqueous solvent. There is no particular limitation on the nature of the solvent to be employed, and any solvent commonly used in a hydrolysis reaction of this type may equally be used in the present invention. The solvent is preferably water or a mixture of water with an organic solvent, such as an alcohol (e.g. methanol, ethanol or propanol) or an ether (such as tetrahydrofuran or dioxane). The base employed is also not critical, provided that is has no effect on other parts of the compound, especially the $\beta$-lactam ring. Preferred bases are alkali metal carbonates, such as sodium carbonate or potassium carbonate. The reaction temperature is also not critical, but we prefer a relatively low temperature, e.g. from 0° C. to about ambient temperature, in order to control side reactions. The time required for the reaction will vary, depending upon the nature of the reagents and on the reaction temperature, but the reaction will normally be complete within from 1 to 6 hours.

When the group represented by $R^7$ contains an aralkyloxycarbonyloxy group (such as a benzyloxycarbonyloxy or p-nitrobenzyloxycarbonyloxy group), it may be removed and the desired group restored by contacting the compound of formula (IV) with a reducing agent. The reducing agent employed and the reaction conditions for this reaction are the same as those in which an aralkyl group serving as the carboxy-protecting group in the group represented by $R^8$ is removed and, accordingly, the carboxy-protecting group and the hydroxy-protecting group may be simultaneously removed by these means. It is also possible by the same reaction, to remove amino-protecting groups in the groups represented by $R^7$ and $R^{11}$ in the compound of formula (IV), particularly aralkyloxycarbonyl groups (such as benzyloxycarbonyl or p-nitrobenzyloxycarbonyl groups) and aralkyl groups (such as benzhydryl groups) to convert the compound of formula (IV) to the corresponding amino compound.

When the group represented by $R^7$ contains a lower alkylsilyloxy group (e.g. a t-butyldimethylsilyloxy group), it may be removed and the desired hydroxy group restored by treating the compound of formula (IV) with tetrabutylammonium fluoride. The reaction is preferably effected in the presence of a solvent, the nature of which is not critical, although we prefer to use ethers, such as tetrahydrofuran or dioxane. The reaction is preferably effected at about ambient temperature and, at this temperature, will normally require from 10 to 18 hours.

When the groups represented by $R^7$ and/or $R^{11}$ in the compound of formula (IV) contain halogenated acetyl groups (such as the trifluoroacetyl or trichloroacetyl groups), which are amino-protecting groups, they may be removed and the free amino group restored by treating the compound of formula (IV) with a base in the presence of an aqueous solvent. The base and solvent employed as well as the reaction conditions are the same as those described above in connection with the removal of a lower aliphatic acyl group represented by $R^7$, which is a hydroxy-protecting group.

Compounds of formula (I) in which Y represents a group of formula $$-\underset{\underset{R^5}{|}}{C}=N-R^6$$

(in which $R^5$ and $R^6$ are as defined above) can be prepared by contacting a compound of formula (I) in which Y represents a hydrogen atom with an imide ester of general formula (VIII):

$$R^{12}O-\underset{\underset{R^5}{|}}{C}=N-R^6 \qquad \text{(VIII)}$$

(in which $R^5$ and $R^6$ are as defined above and $R^{12}$ represents an alkyl group, preferably a lower alkyl group, such as methyl, ethyl, propyl or isopropyl group). This reaction is preferably effected in the presence of a solvent, the nature of which is not critical, although we prefer to use a phosphate buffer solution in order to maintain the pH at a value of about 8. The reaction is preferably carried out at a relatively low temperature, e.g. from 0° C. to about ambient temperature, and will normally require from 10 minutes to 2 hours.

Compounds of formula (I) in which Y represents an aliphatic acyl group can be prepared by reacting a compound of formula (I) in which Y represents a hydrogen atom with a acylating agent. The reaction may be performed under conditions well known for this type of reaction. Where an acid halide (e.g. acetyl chloride or propionyl chloride) is used as the acylating agent, the reaction is preferably effected in the presence of a base (such as triethylamine or pyridine) or in a buffer solution adjusted to a slightly alkaline pH value, e.g. from 8.0 to 8.5. This reaction is preferably effected at a relatively low temperature, e.g. from −20° C. to ambient temperature, and will normally require from 5 minutes to 5 hours.

Where the acylating agent is an acid anhydride (e.g. acetic anhydride or propionic anhydride) or a mixed acid anhydride, such as that which may be obtained from reaction of isovaleric acid or ethyl chlorocarbonate with another carboxylic acid, the reaction conditions (including reaction temperature and reaction time) are similar to those where an acid halide is used as the acylating agent. Alternatively, an active ester may be used as the acylating agent. Examples of such active esters include the p-nitrobenzyl, 2,4,5-trichlorophenyl, cyanomethyl, N-phthaloylimide, N-hydroxysuccinimide, N-hydroxypiperazine, 8-hydroxyquinoline, 2-hydroxyphenyl, 2-hydroxypyridine and 2-pyridylthiol esters of carboxylic acids. Again, the reaction conditions (including reaction temperature and reaction time) are similar to those where an acid halide is used. Other types of acylating agents and methods include, for example: dicyclohexylcarbodiimide; acid azides; carbonyl diimidazole; Woodward's reagent "K"; 2-ethyl-7-hydroxybenzisoxazolium trifluoroborate; 1-ethoxycarbonyl-2-ethoxy-1,2-dihydroxyquinoline; isocyanates; phosphazo compounds; phosphite esters, N-carboxylic anhydrides; and the oxidation/reduction method, usually using dipyridyl disulphide and triphenylphosphine (Chemistry Letters, 1972, 379).

The alternative reaction sequence illustrated by the above reaction scheme comprises:

Step a

As described above, in which the compound of formula (VII) is reacted with an alkanesulphonic acid anhydride, an arenesulphonic acid anhydride, a dialkylphosphoryl halide or a diarylphosphoryl halide in the presence of a base to produce the compound of formula (II);

Step d

In which the resulting compound of formula (II) is reacted with a compound of formula (V) to prepare a compound of formula (VI); and Step e If appropriate, protecting groups are then removed to give the desired compound of formula (I).

The reaction conditions for steps (d) and (e) are essentially the same as those already described for steps (b) and (c), respectively. As already noted, where it is desired to prepare a compound of formula (I) in which Y represents a group of formula $$-\underset{\underset{R^5}{|}}{C}=N-R^6$$

and $R^6$ represents a hydrogen atom, it is preferred to employ a compound of formula (V) in which Y' represents a group of formula

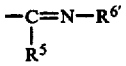

and $R^{6'}$ represents a protecting group for the nitrogen atom. This protecting group may, if required, be deprotected employing the techniques described in relation to the deprotection of similar groups contained in the groups represented by $R^7$ and $R^8$ and, if desired, this deprotection may be carried out simultaneously with or separately from removal of these other protecting groups.

Of the compounds of formula (V), 1-ethyl-3-mercaptopyrrolidine is known, but the other compounds are new and may be prepared, for example, by the process illustrated by the following reaction scheme:

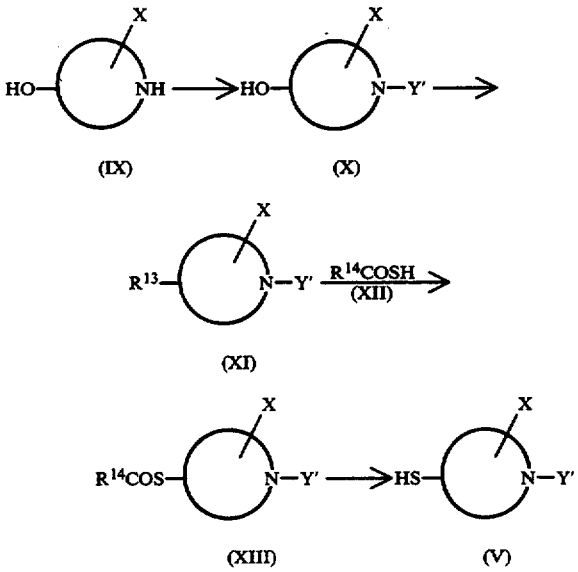

In the above formulae, X, Y' and the group represented by

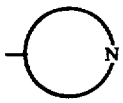

are as defined above, whilst $R^{13}$ represents a leaving group (for example a halogen atom, an alkylsulphonyloxy group, a trihaloalkylsulphonyloxy group or an arylsulphonyloxy group) and $R^{14}$ represents an alkyl group, an aralkyl group or an aryl group.

Introduction of the group Y' to the alicyclic amino group of the compound of formula (IX) to give the compound of formula (X) and formation of the leaving group represented by $R^{13}$ from the hydroxy group of the compound of formula (X) to give the compound of formula (XI) may be performed under conditions well known for this type of reaction.

The compound of formula (XIII) may then be prepared by reacting the compound of formula (XI) with a thiocarboxylic acid, which may be represented by formula (XII):

$$R^{14}COSH \qquad (XII)$$

(in which $R^{14}$ is as defined above). This reaction is preferably effected in an inert solvent and in the presence of a base. The nature of the solvent is not critical, provided that it has no adverse effect on the reaction; suitable solvents include, for example: ethers, such as diethyl ether or tetrahydrofuran; esters, such as ethyl acetate; amides, such as N,N-dimethylformamide or N,N-dimethylacetamide; aromatic hydrocarbons, such as benzene or toluene; dimethyl sulphoxide; and nitromethane. Of course, it is possible to use a mixture of any two or more of these solvents, as well as the individual solvents.

Examples of the base, which may be organic or inorganic, include sodium hydride, lithium hydride, sodium hydroxide, potassium hydroxide, sodium carbonate, potassium carbonate, sodium bicarbonate, triethylamine or diazabicyclononene.

The reaction is normally performed at a temperature which may range from ambient to 100° C. and will generally require from several minutes to 100 hours.

The compound of formula (XIII) thus obtained is then subjected to hydrolysis or solvolysis to give the desired compound of formula (V) or a salt thereof. This reaction is preferably effected in an inert solvent and in the presence of a base. Suitable such solvents include, for example: polar solvents, such as water, methanol or ethanol; water-soluble solvents, such as dioxane or tetrahydrofuran; and mixtures of two or more of these solvents. Examples of the base, which may be organic or inorganic, include sodium hydroxide, potassium hydroxide, sodium methoxide, sodium ethoxide, lithium methoxide, lithium ethoxide, sodium carbonate, potassium carbonate and sodium bicarbonate. There is no particular limitation on the reaction temperature, although we prefer that the reaction should be effected at a relatively low temperature, e.g. from −10° C. to 100° C. The reaction will normally require from several minutes to 10 hours.

Upon completion of the reaction, the compound of formula (V) may be recovered by any conventional means. For example, if it is in the form of a sodium or potassium salt, it may be obtained simply by removing the solvent from the reaction mixture. If it is in the form of the thiol, an acid (e.g. hydrochloric acid or acetic acid) is added to the reaction mixture, followed by a water-immiscible solvent, after which the organic layer is washed with water and the solvent is removed, to give the desired compound. If necessary, the compound may be further purified, for example by recrystallisation, reprecipitation or chromatographic techniques.

Some of the compounds of formula (I) have, in themselves, outstanding antibacterial activity, whilst others, although generally exhibiting some antibacterial activity, are of more value as intermediates for the preparation of other compounds having good antibacterial activity. Those compounds having antibacterial activity exhibit this effect against a wide range of pathogenic microorganisms, including both gram-positive bacteria (such as Staphylococcus aureus) and gram-negative bacteria (such as Escherichia coli, Shigella flexneri, Klebsiella pneumoniae, Proteus vulgaris, Serratia Marcescens, Enterobacter cloacae, Salmonella enteritidis and Pseudomonas aeruginosa) and are thus useful for the treatment of diseases caused by such microorganisms.

The activities of the compounds of the invention, identified by the numbers assigned to them in the foregoing list, against various bacteria are shown in the following Table, in terms of their minimal inhibitory concentrations (μg/ml).

| Microorganism | Compound No. 9 | 2 | 36 | thienamycin |
|---|---|---|---|---|
| Staphylococcus aureus 209P | ≦0.01 | ≦0.01 | ≦0.01 | ≦0.01 |
| Staphylococcus aureus 56 | ≦0.01 | ≦0.01 | ≦0.01 | ≦0.01 |
| Escherichia coli NIHJ | 0.05 | 0.02 | 0.05 | 0.1 |
| Escherichia *coli 609* | 0.05 | 0.02 | 0.05 | 0.1 |
| *Shigella* flexneri 2a | 0.02 | ≦0.01 | 0.05 | 0.1 |
| Pseudomonas aeruginosa | 6.2 | 1.5 | 6.2 | 6.2 |
| Klebsiella pneumoniae 806 | 0.05 | 0.02 | 0.05 | 0.1 |
| Klebsiella pneumoniae 846 | 0.02 | ≦0.01 | 0.02 | 0.1 |
| Proteus vulgaris | 1.5 | 1.5 | 1.5 | 3.1 |
| Salmonella enteritidis G. | 0.05 | 0.05 | 0.05 | 0.2 |
| Serratia marcescens | 0.1 | 0.05 | 0.1 | — |
| Enterobacter cloacae | 0.4 | 0.4 | 0.8 | — |

As can be seen from the above Table, the activities of the compounds of the invention, in the in vitro test, are comparable with or better than the activities of the known compound, thienamycin. However, as already noted, the compounds of the invention show much greater stability in the body than does thienamycin and thus the compounds of the invention exhibit much better activities than thienamycin when tested in vivo. [Moreover, of the compounds disclosed in European Patent Specification No. 17991, the best is said to be N-formimidoyl-thienamycin and we] *We*have found that the above-mentioned compounds of the present invention have better in vivo activity against strains of *Staphylococcus aureus, Escherichia coli, Klebsiella pneumomiae, Proteus vulgaris, Serratia marcescens* and *Pseudomonas aeruginosa* than did N-formimidoylthianemycin. For example, when mice having experimental infections caused by strains of *Staphylococcus aureus* or *Escherichia coli* were treated with 2-(1-acetimidoylpyrrolidin-3-ylthio)-6-(1-hydroxyethyl)-2-carbapenem-3-carboxylic acid (Compound No. 9), and values for its $ED_{50}$ were 0.05 and 1.7 mg/kg, respectively.

It is well known in the art that compounds having a low minimal inhibitory concentration, and which are, as a result, expected to be valuable in chemotherapy, sometimes fail to show a good antibacterial effect when they are administered to humans or other animals. This may be due to various causes, for example chemical or physiological instability of the compounds, poor distribution of the compounds in the body or binding of the compounds to blood serum. The compounds of the invention, however, do not seem to exhibit such problems and thus show a remarkable in vivo activity. This effect is particularly noticeable for those compounds of formula (I) in which Y represents, inter alia, a group of formula

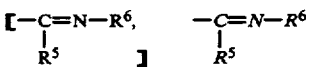

most especially an acetimidoyl group and thus this group of compounds of the invention is of particular interest from the practical point of view.

The compounds of the invention are thus sufficiently stable to warrant their application in therapy and, moreover, they have been found to have a low toxicity to warm-blooded animals. For example, Compound No. 9 was administered by intravenous injection to a group of mice at a dose of 2 g/kg body weight (several orders of magnitude greater than the therapeutic dose)—no mice died.

The compounds of the invention may be administered either orally or parenterally for the treatment of diseases in humans and other animals caused by pathogenic microorganisms. The compounds may be formulated into any conventional forms for administration. For example, for oral administration, suitable formulations include tablets, granules, capsules, powders and syrups, whilst formulations for parenteral administration include injectable solutions for intramuscular or, more preferably intravenous, injection.

The compounds of the invention are preferably administered parenterally, particularly in the form of an intravenous injection.

The dose of the compound of the invention will vary, depending upon the age, body weight and condition of the patient, as well as upon the form and times of administration. However, in general, the adult daily dose is from 200 to 3000 mg of the compound, which may be administered in a single dose or in divided doses.

The invention is further illustrated by the following Examples. Preparation of some of the starting materials is also illustrated in the following Preparations.

EXAMPLE 1 p-Nitrobenzyl (5R, 6S)-6-[1-(R)-hydroxyethyl]-2-(1-p-nitrobenzyloxycarbonylpyrrolidin-3-ylthio)-2-carbapenem-3-carboxylate (Compound No. 15)

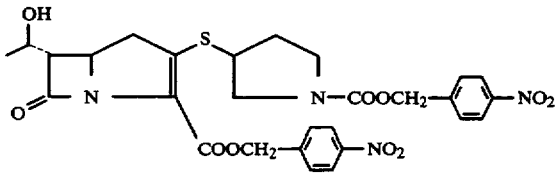

To a solution of 2.24 g of p-nitrobenzyl (5R, 6S)-6-[1-(R)-hydroxyethyl]-2-oxocarbapenem-3-carboxylate in 20 ml of acetonitrile were added 1.35 ml of diisopropylethylamine and 1.58 ml of diphenylphosphoryl chloride, with ice-cooling, under a stream of nitrogen gas. The mixture was then stirred at that temperature for 30 minutes, after which 1.23 ml of diisopropylethylamine and 2.00 g of N-p-nitrobenzyloxycarbonyl-3-mercaptopyrrolidine were added. The resulting mixture was then stirred for a further 1 hour. The crystals which separated were collected by filtration, washed with a small amount of acetonitrile and then dried to give 2.54 g of the desired product in a crude form.

Meanwhile the filtrate was diluted with ethyl acetate, washed, in turn, with a saturated aqueous solution of sodium chloride, a 5% w/v aqueous solution of sodium bicarbonate and a saturated aqueous solution of sodium chloride and then dried over anhydrous magnesium sulphate. The solvent was distilled off and a small amount of ethyl acetate was added to the resulting residue. The precipitated crystals were collected by filtration to give a further 0.94 g of the desired product. The filtrate was then concentrated by evaporation under reduced pressure and the resulting residue was purified by column chromatography through silica gel eluted with ethyl acetate to give an additional 27 mg of the desired product. The total yield of the desired product was 89%.

Infrared Absorption Spectrum (KBr) $\nu_{max}$ $cm^{-1}$: 3560, 1780, 1705.

Nuclear Magnetic Resonance Spectrum ($CDCl_3$) δppm: 1.35 (3H, doublet, J=6.0 Hz); 1.8–2.9 (3H, multiplet); 3.1–4.6 (10H, multiplet); 5.23 (2H, singlet); 5.23, 5.50 (2H, AB-quartet, J=14 Hz); 7.53, 8.20 (4H, $A_2B_2$, J=9.0 Hz); 7.65, 8.20 (4H, $A_2B_2$, J=9.0 Hz).

EXAMPLE 2

(5R, 6S)-6-[1-(R)-Hydroxyethyl]-2-(pyrrolidin-3-ylthio)-2-carbapenem-3-carboxylic acid (Compound No. 2)

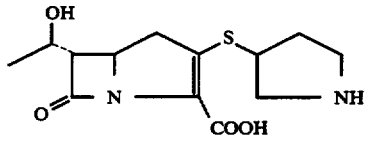

1.0 g of platinum oxide and 80 ml of water were placed in a 2 liter flask and shaken for 15 minutes under hydrogen atmosphere. The water was then decanted off and discarded. 5.0 g of p-nitrobenzyl (5R, 6S)-6-[1-(R)-hydroxyethyl]-2-(1-p-nitrobenzyloxycarbonylpyrrolidin-3-ylthio)-2-carbapenem-3-carboxylate and 400 ml of tetrahydrofuran were added and dissolved by shaking the whole mixture. 400 ml of a phosphate buffer solution (0.1M, pH 7.0) were then added and the resulting mixture was shaken vigorously for 1.5 hours under a hydrogen atmosphere.

At the end of this time, the catalyst was removed by filtration and then the tetrahydrofuran was distilled from the filtrate to give a precipitate, which was removed by filtration. The filtrate was extracted with ethyl acetate and the residual aqueous layer was concentrated by evaporation in a vacuum. The residue from the aqueous layer was purified by chromatography through a column containing Diaion HP-20AG (Mitsubishi Chemical Industries Co. Ltd.), eluted with a 5% v/v aqueous acetone, to give 1.8 g (yield 74%) of the desired compound.

Infrared Absorption Spectrum (KBr) $\nu_{max}$ $cm^{-1}$: 3400, 1770, 1590.

Ultraviolet Absorption Spectrum ($H_2O$) $\lambda_{max}$ nm (ε): 298 (7290).

Nuclear Magnetic Resonance Spectrum ($D_2O$) δppm: 1.27 (3H, doublet, J=6.5 Hz); 1.8–2.2 (1H, multiplet); 2.3–2.7 (1H, multiplet); 3.19 (2H, doublet, J=9.5 Hz); 3.3–3.8 (5H, multiplet); 3.9–4.4 (3H, multiplet).

EXAMPLE 3 p-Nitrobenzyl (5R, 6S)-6-[1-(R)-hydroxyethyl]-2-(1-p-nitrobenzyloxycarbonylazetidin-3-ylthio)-2-carbapenem-3-carboxylate

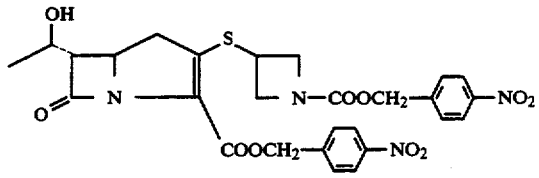

The procedure described in Example 1 was repeated, but using 60 mg of p-nitrobenzyl (5R, 6S)-6-[1-(R)-hydroxyethyl]-2-oxocarbapenam-3-carboxylate, 66 μl of diisopropylethylamine, 38 μl of diphenylphosphoryl chloride and 51 mg of N-p-nitrobenzyloxycarbonyl-3-mercaptoazetidine, to give 81 mg of the title compound.

Infrared Absorption Spectrum (KBr) $\nu_{max}$ $cm^{-1}$: 3450, 1780, 1730.

Nuclear Magnetic Resonance Spectrum (heptadeuterated dimethylformamide) δppm: 1.22 (3H, doublet, J=6.0 Hz); 3.0–4.8 (11H, multiplet); 5.28 (2H, singlet); 5.35, 5.58 (2H, AB-quartet, J=14.5 Hz); 7.68, 8.27 (4H, $A_2B_2$, J=8.5 Hz); 7.81, 8.27 (4H, $A_2B_2$, J=8.5 Hz).

EXAMPLE 4

(5R, 6S)-2-(Azetidin-3-ylthio)-6-[1-(R)-hydroxyethyl]-2-carbapenem-3-carboxylic acid (Compound No. 1)

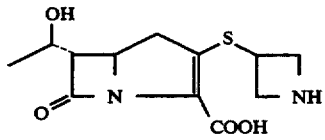

The procedure described in Example 2 was repeated, but using 20 mg of platinum oxide, 81 mg of p-nitrobenzyl (5R, 6S)-6-[1-(R)-hydroxyethyl]-2-(1-p-nitrobenzyloxycarbonylazetidin-3-ylthio)-2-carbapenem-3-carboxylate, 4 ml of a 0.1M phosphate buffer solution (pH=7.0), 6 ml of water and 10 ml of tetrahydrofuran, to give 17 mg of the title compound.

Infrared Absorption Spectrum (KBr) $\nu_{max}$ $cm^{-1}$: 3400, 1760, 1605.

Ultraviolet Absorption Spectrum ($H_2O$) $\lambda_{max}$ nm (ε): 299 (5970).

Nuclear Magnetic Resonance Spectrum ($D_2O$) δppm: 1.27 (3H, doublet, J=6.5 Hz); 3.04 (2H, doublet, J=10.0 Hz); 3.38 (1H, doubled doublet, J=3.0 & 6.0 Hz); 3.7–5.1 (7H, multiplet).

EXAMPLE 5 p-Nitrobenzyl (5R, 6S)-6-[1-(R)-hydroxyethyl]-2-(1-p-nitrobenzyloxycarbonylpiperidin-4-ylthio)-2-carbapenem-3-carboxylate

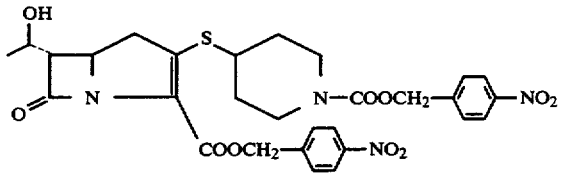

The procedure described in Example 1 was repeated, but using 30 mg of p-nitrobenzyl (5R, 6S)-6-[1-(R)-hydroxyethyl]-2-oxocarbapenam-3-carboxylate, 34 μl of diisopropylethylamine, 19 μl of diphenylphosphoryl chloride and 84 mg of N-p-nitrobenzyloxycarbonyl-4-mercaptopiperidine, to give 45 mg of the title compound.

Infrared Absorption Spectrum KBr) $\nu_{max}$ $cm^{-1}$: 3450, 1780, 1710.

Nuclear Magnetic Resonance Spectrum (heptadeuterated dimethylformamide) δ ppm: 1.23 (3H, doublet, J=6.5 Hz); 1.5–4.5 (15H, multiplet); 5.25 (2H, singlet); 5.26, 5.51 (2H, AB-quartet, J=14.5 Hz); 7.63, 8.22 (4H, $A_2B_2$, J=8.5 Hz); 7.76, 8.22 (4H, $A_2B_2$, J=8.5 Hz).

EXAMPLE 6

(5R, 6S)-6-[1-(R)-Hydroxyethyl]-2-(piperidin-4-ylthio)-2-carbapenem-3-carboxylic acid (Compound No. 4)

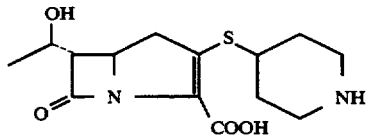

The procedure described in Example 4 was repeated, but using 42 mg of p-nitrobenzyl (5R, 6S)-6-[1-(R)-hydroxyethyl]-2-(1-p-nitrobenzyloxycarbonylpiperidin-4-ylthio)-2-carbapenem-3-carboxylate, to give 9 mg of the title compound.

Infrared Absorption Spectrum (KBr) $\nu_{max}$ $cm^{-1}$: 3430, 1765, 1595.

Ultraviolet Absorption Spectrum ($H_2O$) $\lambda_{max}$ nm (ε): 299 (7450).

Nuclear Magnetic Resonance Spectrum ($D_2O$) δ ppm: 1.29 (3H, doublet, J=6.0 Hz); 1.7–2.4 (4H, multiplet); 2.9–3.6 (7H, multiplet); 4.0–4.4 (3H, multiplet).

EXAMPLE 7

(5R, 6S)-2-(1-Formimidoylpyrrolidin-3-ylthio)-6-[1-(R)-hydroxyethyl]-2-carbapenem-3-carboxylic acid (Compound No. 27)

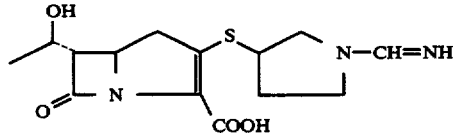

80 mg of (5R, 6S)-6-[1-(R)-hydroxyethyl]-2-(pyrrolidin-3-ylthio)-2-carbapenem-3-[caboxylic] *carboxylic* acid were dissolved in 12 ml of a phosphate buffer solution (pH=7.1) and the pH of the resulting solution was adjusted to a value of 8.5 by the addition of a 1N aqueous solution of sodium hydroxide, with ice-cooling. 129 mg of methyl formimidate hydrochloride were then added to this solution and the resulting mixture was then adjusted to a pH value of 8.5 by the addition of a further quantity of an aqueous solution of sodium hydroxide. The mixture was stirred, with ice-cooling, for 10 minutes, after which the pH value of the resulting solution was adjusted to 7.0 by the addition of 1N hydrochloric acid. The solution was then subjected to column chromatography through Diaion HP-20 AG, eluted with a 5% v/v aqueous acetone solution, to give 64 mg of the title compound.

Ultraviolet Absorption Spectrum ($H_2O$) $\lambda_{max}$ nm(ε): 297 (7920).

Infrared Absorption Spectrum (KBr) $\nu_{max}$ $cm^{-1}$: 3400, 1765, 1590.

Nuclear Magnetic Resonance Spectrum ($D_2O$) δ ppm: 1.30 (3H, doublet, J=6.0 Hz); 1.8–2.8 (2H, multiplet); 3.21 (2H, doublet-like, J=9.0 Hz); 3.45 (1H, doubled doublet, J=3.0 & 6.0 Hz); 3.3–4.4 (7H, multiplet); 8.00 (1H, singlet).

EXAMPLE 8

(5R, 6S)-2-(1-Acetimidoylpyrrolidin-3-ylthio)-6-[1-(R)-hydroxyethyl]-2-carbapenem-3-carboxylic acid (Compound No. 9)

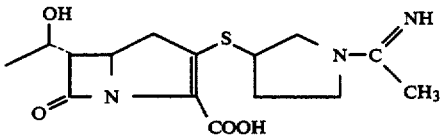

63 mg of (5R, 6S)-6-[1-(R)-hydroxyethyl]-2-(pyrrolidin-3-ylthio)-2-carbapenem-3-carboxylic acid were dissolved in 9 ml of a phosphate buffer solution (pH=7.1), and then the pH of the solution was adjusted to a value of 8.5 by the addition, with ice-cooling, of a 1N aqueous solution of sodium hydroxide. 121 mg of ethyl acetimidate hydrochloride were then added and the pH of the mixture was again adjusted to a value of 8.5 by the addition of a 1N aqueous solution of sodium hydroxide. The mixture was stirred, with ice-cooling, for 10 minutes, after which its pH value was adjusted to 7.0 by the addition of 1N hydrochloric acid. The mixture was then purified by passing it through a column of Diaion HP-20 AG, and eluting the column with a 5% v/v aqueous solution of acetone. The eluent was lyophilized, giving 42 mg of the title compound. This was further purified by high performance liquid chromatography (μBondapak $C_{18}$, eluted with a 1:10 by volume mixture of tetrahydrofuran and water), to give 38 mg of a further purified product.

Ultraviolet Absorption Spectrum ($H_2O$) $\lambda_{max}$ nm (ε): 298 (8960).

Infrared Absorption Spectrum (KBr) $\nu_{max}$ $cm^{-1}$: 3400, 1760, 1675.

Nuclear Magnetic Resonance Spectrum ($D_2O$) δ ppm: 1.29 (3H, doublet, J=6.5 Hz); 1.8–2.7 (2H, multiplet); 2.29 (3H, singlet); 3.23 (2H, doublet-like, J=9.5

Hz); 3.44 (1H, doubled doublet, J=3.0 & 6.0 Hz); 3.3–4.4 (7H, multiplet).

EXAMPLE 9

Sodium (5R, 6S)-2-(1-acetylpyrrolidin-3-ylthio)-6-[1-(R)-hydroxyethyl]-2-carbapenem-3-carboxylate (Compound No. 28)

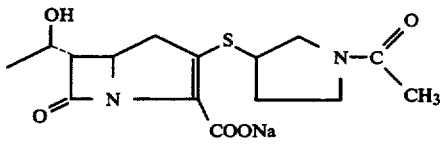

A solution of 80 mg of (5R, 6S)-6-[1-(R)-hydroxyethyl]-2-(pyrrolidin-3-ylthio)-2-carbapenem-3-carboxylic acid in 7 ml of a 0.1 M phosphate buffer solution (pH=7.0) was ice-cooled and then its pH was adjusted to a value of 8.5 by the addition of a 1N aqueous solution of sodium hydroxide. 150 μl of acetic anhydride were then added to the solution, whose pH was again adjusted to a value of 8.5 by the addition of a 1N aqueous solution of sodium hydroxide. The mixture was then stirred, with ice-cooling, for 15 minutes, after which it was neutralized to pH 7.0 by the addition of 5% w/v hydrochloric acid. The mixture was then purified by chromatography through a column containing Diaion HP-20 AG, eluted with a 5% v/v aqueous solution of acetone. The eluent was then freeze-dried, to give 40 mg of the title compound in the form of a colourless powder.

Ultraviolet Absorption Spectrum ($H_2O$) $\lambda_{max}$ nm (ε): 300 (8500).

Infrared Absorption Spectrum (KBr) $\nu_{max}$ $cm^{-1}$: 3420, 1750, 1600.

Nuclear Magnetic Resonance Spectrum ($D_2O$) δ ppm: 1.29 (3H, doublet, J=6.5 Hz); 2.07 (3H, singlet); 1.9–2.7 (2H, multiplet); 3.23 (2H, doublet, J=9.5 Hz); 3.42 (1H, doubled doublet, J=3.0 & 6.0 Hz); 3.4–4.4 (7H, multiplet).

EXAMPLE 10 p-Nitrobenzyl (5R, 6S)-6-[1-(R)-acetoxyethyl]-2-(1-p-nitrobenzyloxycarbonylpyrrolidin-3-ylthio)-2-carbapenem-3-carboxylate

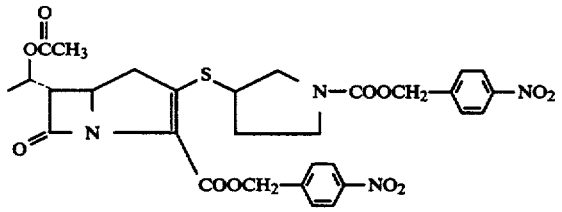

To a suspension of 1.00 g of p-nitrobenzyl (5R, 6S)-6-[1-(R)-hydroxyethyl]-2-(1-p-nitrobenzyloxycarbonylpyrrolidin-3-ylthio)-2-carbapenem-3-carboxylate in 22 ml of methylene chloride were added, with ice-cooling and under a stream of nitrogen, 20 mg of 4-dimethylaminopyridine, 684 μl of triethylamine and 348 μl of acetic anhydride. The mixture was stirred at room temperature for 1 hour, after which the methylene chloride was distilled off and the residue was extracted with ethyl acetate. The extract was washed, in turn, with 5% w/v hydrochloric acid, a 5% w/v aqueous solution of sodium bicarbonate, water and a saturated aqueous solution of sodium chloride, after which it was dried over anhydrous magnesium sulphate. The solvent was then distilled off under reduced pressure and the residue was washed with diethyl ether, to give 994 mg of the title compound in the form of colourless crystals.

Infrared Absorption Spectrum (Nujol-trade mark) $\nu_{max}$ $cm^{-1}$: 1775, 1735, 1705, 1690.

Nuclear Magnetic Resonance Spectrum ($CDCl_3$) δ ppm: 1.39 (3H, doublet, J=6.0 Hz); 2.03 (3H, singlet); 1.7–2.5 (2H, multiplet); 3.0–4.4 (10H, multiplet); 5.20 (2H, singlet); 5.21, 5.46 (2H, AB-quartet, J=14.0 Hz); 7.48, 8.18 (4H, $A_2B_2$, J=9.0 Hz); 7.62, 8.18 (4H, $A_2B_2$, J=9.0 Hz).

EXAMPLE 11

(5R, 6S)-6-[1-(R)-Acetoxyethyl]-2-(pyrrolidin-3-ylthio)-2-carbapenem-3-carboxylic acid (Compound No. 47)

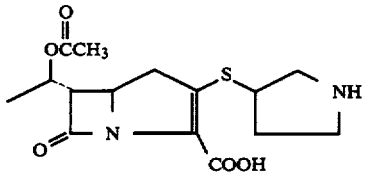

Substantially the same procedure as is described in Example 2 was repeated, except that 950 mg of p-nitrobenzyl (5R, 6S)-6-[1-(R)-acetoxyethyl]-2-(1-p-nitrobenzyloxycarbonylpyrrolidin-3-ylthio)-2-carbapenem-3-carboxylate were employed, to give 111 mg of the desired product in the form of colourless, amorphous crystals.

Ultraviolet Absorption Spectrum ($H_2O$) $\lambda_{max}$ nm: 301.

Nuclear Magnetic Resonance Spectrum ($D_2O$) δ ppm: 1.30 (3H, doublet, J=6.0 Hz); 2.06 (3H, singlet); 1.8–2.9 (2H, multiplet); 3.16 (2H, doublet, J=9.0 Hz); 3.0–4.4 (8H, multiplet).

EXAMPLE 12

(5R, 6S)-2-(1-Acetimidoylpyrrolidin-3-ylthio)-6-[1-(R)-acetoxyethyl]-2-carbapenem-3-carboxylic acid (Compound No. 25)

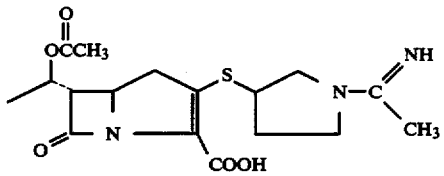

To a solution of 109 mg of (5R, 6S)-6-[1-(R)-acetoxyethyl]-2-(pyrrolidin-3-ylthio)-2-carbapenem-3-carboxylic acid in 15 ml of a 0.1M phosphate buffer solution (pH=7.0) was added, whilst ice-cooling, sufficient of a 1N aqueous solution of sodium hydroxide to adjust the pH to a value of 8.5. 199 mg of ethyl acetimidate hydrochloride were then added to the solution, whose pH was again adjusted to a value of 8.5 by the addition of a 1N aqueous solution of sodium hydroxide. After stirring the mixture, with ice-cooling, for 10 minutes, its pH was adjusted to a value of 7.0 by the addition of 1N hydrochloric acid. The mixture was then purified by column chromatography through Diaion HP-20 AG, eluted with a 5% v/v aqueous solution of acetone. The eluent was freeze-dried, to give 80 mg of the desired product in the form of colourless, amorphous crystals.

Nuclear Magnetic Resonance Spectrum ($D_2O$) δ ppm: 1.36 (3H, doublet, J=6.0 Hz); 2.14 (3H, singlet); 2.29 (3H, singlet); 2.1–2.8 (2H, multiplet); 3.24 (2H, doublet, J=9.0 Hz); 3.3–4.4 (8H, multiplet).

EXAMPLE 13 p-Nitrobenzyl (5R, 6S)-6-[1-(R)-hydroxyethyl]-2-(4-methylthio-1-p-nitrobenzyloxycarbonylpyrrolidin-3-ylthio)-2-carbapenem-3-carboxylate

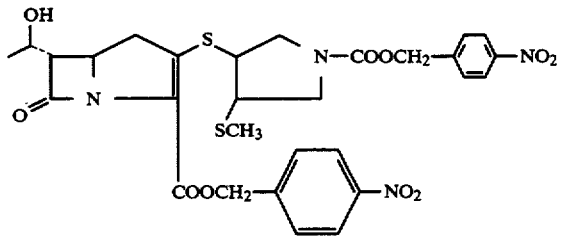

To a solution of 60 mg of p-nitrobenzyl (5R, 6S)-6-[1-(R)-hydroxyethyl]-2-oxocarbapenam-3-carboxylate in 3 ml of acetonitrile were added, with ice-cooling and under a stream of nitrogen, 37 μl of diisopropylethylamine and 42 μl of diphenylphosphoryl chloride. The mixture was then stirred, whilst ice-cooling, for 30 minutes, after which 40 μl of diisopropylethylamine and 62 mg of 3-mercapto-4-methylthio-1-p-nitrobenzyloxycarbonylpyrrolidine were added, and then stirring was continued for a further 1 hour. The reaction mixture was then diluted with ethyl acetate and washed, in turn, with water and with a saturated aqueous solution of sodium chloride, after which it was dried over anhydrous magnesium sulphate. The solvent was distilled off and the resulting residue was purified by chromatography through a Lobar column, eluted with a 3:1 by volume mixture of ethyl acetate and cyclohexane, to give 67 mg of the title compound (a mixture of stereoisomers), in the form of an oil.

Infrared Absorption Spectrum ($CHCl_3$) $\nu_{max}$ $cm^{-1}$: 1780, 1700.

Nuclear Magnetic Resonance spectrum ($CDCl_3$) δ ppm: 1.32 (3H, doublet, J=6.0 Hz); 2.22 (3H, singlet); 2.4–4.5 (12H, multiplet); 5.25 (2H, singlet); 5.22, 5.53 (2H, AB-quartet, J=14.0 Hz); 7.55, 8.22 (4H, $A_2B_2$, J=9.0 Hz); 7.67, 8.22 (4H, $A_2B_2$, J=9.0 Hz).

EXAMPLE 14 p-Nitrobenzyl (5R, 6S)-6-[1-(R)-hydroxyethyl]-2-(4-methylsulphinyl-1-p-nitrobenzyloxycarbonylpyrrolidin-3-ylthio)-2-carbapenem-3-carboxylate

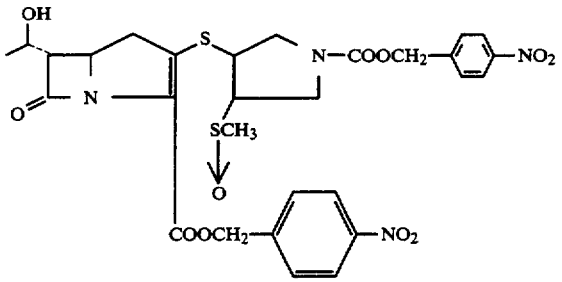

Essentially the same procedure as is described in Example 13 was repeated, except that 60 mg of p-nitrobenzyl (5R, 6S)-6-[1-(R)-hydroxyethyl]-2-oxocarbapenam-3-carboxylate, 79 μl of diisopropylethylamine, 42 μl of diphenylphosphoryl chloride and 120 mg of 3-mercapto-4-methylsulphinyl-1-p-nitrobenzyloxycarbonylpyrrolidine were used, to give a crude product. This was then purified by column chromatography through silica gel, eluted with a 20:1 by volume mixture of ethyl acetate and methanol, to give 75 mg of the title compound as a mixture of stereoisomers.

In frared Absorption Spectrum ($CHCl_3$) $\nu_{max}$ $cm^{-1}$: 3400, 1775, 1705.

Nuclear Magnetic Resonance Spectrum ($CDCl_3$) δ ppm: 1.31 (3H, doublet, J=6.5 Hz); 2.58 (3H, singlet); 2.6–4.5 (12H, multiplet); 5.22 (2H, singlet); 5.20, 5.45 (2H, AB-quartet, J=14.0 Hz); 7.49, 8.16 (4H, $A_2B_2$, J=9.0 Hz); 7.61, 8.16 (4H, $A_2B_2$, J=9.0 Hz).

EXAMPLE 15 p-Nitrobenzyl (5R, 6S)-6-[1-(R)-hydroxyethyl]-2-(4-methoxy-1-p-nitrobenzyloxycarbonylpyrrolidin-3-ylthio)-2-carbapenem-3-carboxylate

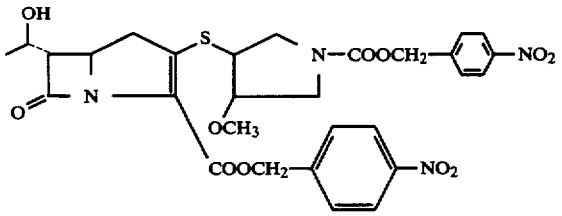

Essentially the same procedure as is described in Example 13 was repeated, except that 60 mg of p-nitrobenzyl (5R, 6S)-6-[1-(R)-hydroxyethyl]-2-oxocarbapenam-3-carboxylate, 73 μl of diisopropylethylamine, 38 μl of diphenylphosphoryl chloride and 60 mg of 3-mercapto-4-methoxy-1-p-nitrobenzyloxycarbonylpyrrolidine were used, to give 46 mg of the desired compound (a mixture of stereoisomers) in the form of an oil.

Infrared Absorption Spectrum ($CHCl_3$) $\nu_{max}$ $cm^{-1}$: 3400, 1780, 1705.

Nuclear Magnetic Resonance Spectrum ($CDCl_3$) δ ppm: 1.31 (3H, doublet, J=6.5 Hz); 2.6–4.5 (12H, multiplet); 3.40 (3H, singlet); 5.21, 5.50 (2H, AB-quartet, J=14.0 Hz); 5.22 (2H, singlet); 7.55, 8.22 (4H, $A_2B_2$, J=9.0 Hz); 7.68, 8.22 (4H, $A_2B_2$, J=9.0 Hz).

EXAMPLE 16

(5R, 6S)-6-[1-(R)-Hydroxyethyl]-2-(4-methylthiopyrrolidin-3-ylthio)-2-carbapenem-3-carboxylic acid (Compound No. 48)

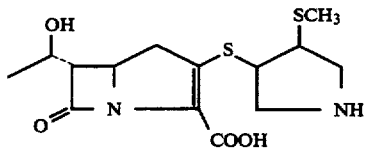

To a solution of 67 mg of p-nitrobenzyl (5R, 6S)-6-[1-(R)-hydroxyethyl]-2-(4-methylthio-1-p-nitrobenzyloxycarbonylpyrrolidin-3-ylthio)-2-carbapenem-3-carboxylate in 8 ml of tetrahydrofuran were added 8 ml of a 0.1M phosphate buffer solution (pH=7.0) and 14 mg of a platinum oxide catalyst. The mixture was then subjected to hydrogenation for 1.5 hours in a Parr shaker, under a hydrogen gauge pressure of 2.8 bars (40 psi). At the end of this time, the catalyst was removed by filtration and the tetrahydrofuran was distilled off. The insolubles which were thus precipitated were removed by filtration and the filtrate was washed with ethyl acetate. The resulting aqueous residue was concentrated by evaporation under reduced pressure.

The residue was then passed through a column containing Diaion HP-20 P (Mitsubishi Chemical Industries Co. Ltd,), eluted with a 5% v/v aqueous solution of acetone, to give 13 mg of the desired compound in the form of colourless, amorphous crystals.

Ultraviolet Absorption Spectrum ($H_2O$) $\lambda_{max}$ nm ($\epsilon$): 297 (7500).

Infrared Absorption Spectrum (KBr) $\nu_{max}$ $cm^{-1}$: 3430, 1765, 1595.

Nuclear Magnetic Resonance Spectrum ($D_2O$) $\delta$ ppm: 1.32 (3H, doublet, J=6.5 Hz); 2.5 (3H, singlet); 3.23 (2H, doublet, J=9.0 Hz); 3.45 (1H, doubled doublet, J=2.5 & 6.0 Hz); 3.1–4.4 (8H, multiplet).

EXAMPLE 17

(5R, 6S)-6-[1-(R)-Hydroxyethyl]-2-(4-methylsulphinylpyrrolidin-3-ylthio)-2-carbapenem-3-carboxylic (Compound No. 49)

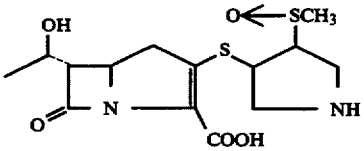

Essentially the same procedure as is described in Example 16 was repeated, except that 75 mg of p-nitrobenzyl (5R, 6S)-6-[1-(R)-hydroxyethyl]-2-(4-methylsulphinyl-1-p-nitrobenzyloxycarbonylpyrrolidin-3-ylthio)-2-carbapenem-3-carboxylate were used, to give 13 mg of the desired product (a mixture of stereoisomers), in the form of colourless, amorphous crystals.

Ultraviolet Absorption Spectrum ($H_2O$) $\lambda_{max}$ nm ($\epsilon$): 297 (7100).

Infrared Absorption Spectrum (KBr) $\nu_{max}cm^{-1}$: 3420, 1750, 1595.

Nuclear Magnetic Resonance Spectrum ($D_2O$) $\delta$ppm: 1.32 (3H, doublet, J=6.5 Hz); 2.88 (3H, singlet); 3.1–4.5 (1OH, multiplet); 3.47 (1H, doubled doublet, J=3.0 & 6.0 Hz).

EXAMPLE 18

(5R, 6S)-6-[1-(R)-Hydroxyethyl]-2-(4-methoxypyrrolidin-3-ylthio)-2-carbapenem-3-carboxylic acid (Compound No. 50)

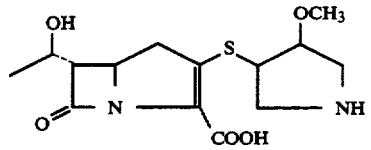

Essentially the same procedure as is described in Example 16 was repeated, except that 46 mg of p-nitrobenzyl (5R, 6S)-6-[1-(R)-hydroxyethyl]-2-(4-methoxy-1-p-nitrobenzyloxycarbonylpyrrolidin-3-ylthio)-2-carbapenem-3-carboxylate were used, to give 3 mg of the title compound (a mixture of stereoisomers), in the form of colourless, amorphous crystals.

Ultraviolet Absorption Spectrum ($H_2O$) $\lambda_{max}$ nm: 297.

Infrared Absorption Spectrum (KBr) $\nu_{max}$ $cm^{-1}$: 3450, 1750, 1595.

Nuclear Magnetic Resonance Spectrum ($D_2O$) $\delta$ppm: 1.38 (3H, doublet, J=6.0 Hz); 3.1–4.6 (11H, multiplet); 3.43 (3H, singlet).

EXAMPLE 19 p-Nitrobenzyl (5R, 6S)-6-[1-(R)-hydroxyethyl]-2-[1-(N-p-nitrobenzyloxycarbonylacetimidoyl)pyrrolidin-3-ylthio]-2-carbapenem-3-carboxylate

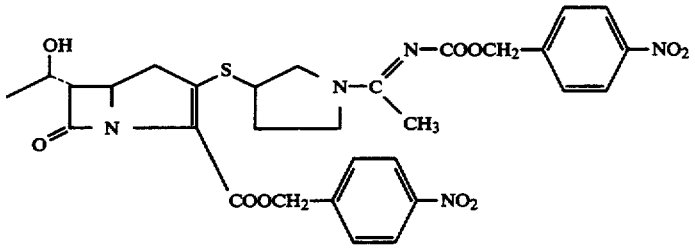

To a solution of 1.5 g of p-nitrobenzyl (5R, 6S)-6-[1-(R)-hydroxyethyl]-2-oxocarbapenam-3-carboxylate in 70 ml of aqueous acetonitrile were added, with ice-cooling and under a stream of nitrogen, 0.82 ml of diisopropylethylamine and 0.96 ml of diphenylphosphoryl chloride. The mixture was then stirred, with ice-cooling, for 30 minutes, after which a further 0.82 ml of diisopropylethylamine were added, together with 1.5 g of 1-(N-p-nitrobenzyloxycarbonylacetimidoyl)-3-mercaptopyrrolidine, and then the resulting mixture was stirred for 1 hour. At the end of this time, the mixture was diluted with ethyl acetate and then washed, in turn, with a saturated aqueous solution of sodium chloride, with a 5% w/v aqueous solution of sodium bicarbonate and with a saturated aqueous solution of sodium chloride, after which it was dried over anhydrous magnesium sulphate. The solvent was then distilled off under reduced pressure and a small amount of ethyl acetate was added to the residue to precipitate crystals.

These crystals were collected by filtration, to give 1.6 g of the title compound. The mother liquor was purified by chromatography through a Lobar column containing silica gel, eluted with ethyl acetate, to give a further 0.3 g of the title compound.

Nuclear Magnetic Resonance Spectrum ($CDCl_3$) δppm: 1.35 (3H, doublet, J=6.0 Hz); 1.8–2.9 (3H, multiplet); 2.30 (3H, singlet); 3.1–4.6 (10H, multiplet); 5.25 (2H, singlet); 5.2, 5.5 (2H, AB-quartet, J=14 Hz); 7.5, 8.2 (4H, $A_2B_2$, J=9.0 Hz); 7.6, 8.2 (4H, $A_2B_2$, J=9.0 Hz).

EXAMPLE 20

(5R, 6S)-2-(1-Acetimidoylpyrrolidin-3-ylthio)-6-[1-(R)-hydroxyethyl]-2-carbapenem-3-carboxylic acid

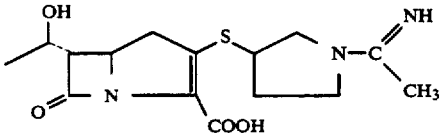

To a solution of 1.9 g of p-nitrobenzyl (5R, 6S)-6-[1-(R)-hydroxyethyl]-2-[1-(N-p-nitrobenzyloxycarbonylacetimidoyl)pyrrolidin-3-ylthio]-2-carbapenem-3-carboxylate in 200 ml of tetrahydrofuran were added 200 ml of a morpholinopropanesulphonic acid buffer solution (pH=7.0) and 350 mg of a platinum oxide catalyst and the mixture was hydrogenated for 1 hour. The catalyst was then filtered off and the tetrahydrofuran was removed by distillation under reduced pressure. The insolubles which precipitated were filtered off and the filtrate was washed with ethyl acetate. The resulting aqueous layer was concentrated by evaporation under reduced pressure and the concentrate was purified by chromatography through a column of Diaion HP-20 AG, eluted with a 5% v/v aqueous solution of acetone, to give 0.4 g of the title compound, whose properties were identical with those reported in Example 8.

EXAMPLE 21

Following substantially the same procedures as are described in Examples 19 and 20, the following compounds were also obtained:

(5R, 6S)-6-[1-(R)-Hydroxyethyl]-2-(3,4,5,6-tetrahydropyrimidin-5-ylthio)-2-carbapenem-3-carboxylic acid (Compound No. 51)

Infrared Absorption Spectrum (KBr) $\nu_{max}$ $cm^{-1}$: 3400, 1765, 1670, 1600.

Nuclear Magnetic Resonance Spectrum ($D_2O$) δppm: 1.30 (3H, doublet, J=6.0 Hz); 3.23 (2H, doubled doublet, J=9.0 & 4.0 Hz); 3.46 (1H, doubled doublet, J=7.0 & 2.0 Hz); 3.68–3.96 (5H, multiplet); 4.13–4.40 (2H, multiplet); 8.04 (1H, singlet).

(5R, 6S)-6-[1-(R)-Hydroxyethyl]-2-(2-methyl-3,4,5,6-tetrahydropyrimidin-5-ylthio)-2-carbapenem-3-carboxylic acid Infrared Absorption Spectrum (KBr) $\nu_{max}$ $cm^{-1}$: 3400, 1765, 1660, 1590.

Nuclear Magnetic Resonance Spectrum ($D_2O$) δppm: 1.29 (3H, doublet, J=6.0 Hz); 2.23 (3H, singlet); 3.22 (2H, doubled doublet, J=9.0 & 3.0 Hz); 3.45 (1H, doubled doublet, J=6.0 & 3.0 Hz); 3.6–3.9 (5H, multiplet); 4.1–4.4 (2H, multiplet).

(5R, 6S)-2-(2-Ethyl-3,4,5,6-tetrahydropy rimidin-5-ylthio)-6-[1-(R)-hydroxyethyl]-2-carbapenem-3-carboxylic acid Infrared Absorption Spectrum (KBr) $\nu_{max}$ $cm^{-1}$: 3400, 1760, 1650, 1590.

Nuclear Magnetic Resonance Spectrum ($D_2O$) δppm: 1.24 (3H, triplet, J=7.5 Hz); 1.29 (3H, doublet, J=6.0 Hz); 2.52 (2H, quartet, J=7.5 Hz); 3.23 (2H, doubled doublet, J=9.0 & 4.0 Hz); 3.34–3.60 (2H, multiplet); 3.62–3.94 (4H, multiplet); 4.09–4.40 (2H, multiplet).

(5R, 6S)-6-[1-(R)-Hydroxyethyl]-2-(2-methoxymethyl-3,4,5,6-tetrahydropyrimidin-5-ylthio)-2-carbapenem-3-carboxylic acid Ultraviolet Absorption Spectrum ($H_2O$) $\lambda_{max}$ nm (ε): 295.4 (8100).

Infrared Absorption Spectrum (KBr) $\nu_{max}$ $cm^{-1}$: 3350, 1755, 1660, 1580.

Nuclear Magnetic Resonance Spectrum ($D_2O$) δppm: 1.28 (3H, doublet, J=6.0 Hz); 3.22 (2H, doubled doublet, J=9.0 & 4.0 Hz); 3.47 (3H, singlet); 3.38–3.62 (2H, multiplet); 3.69–3.94 (4H, multiplet); 4.07–4.40 (2H, multiplet); 4.38 (2H, singlet).

(5R, 6S)-2-(2-Cyanomethyl-3,4,5,6-tetrahydropyrimidin-5-ylthio)-6-[1-(R)-hydroxyethyl]-2-carbapenem-3-carboxylic acid (Compound No. 52)

Infrared Absorption Spectrum (KBr) $\nu_{max}$ $cm^{-1}$: 3400, 2300, 1760, 1660, 1600.

PREPARATION 1

3-Hydroxy-1-(N-p-nitrobenzyloxycarbonylacetimidoyl)pyrrolidine

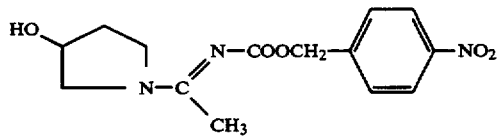

To a suspension of 12.3 g of 3-hydroxypyrrolidine hydrochloride in 100 ml of ethanol were added 14 ml of triethylamine, followed by 12.3 g of ethyl acetimidate hydrochloride; the mixture was then stirred at room temperature for 1 hour. At the end of this time, the solvent was distilled off under reduced pressure, and then 100 ml of methylene chloride were added to the residue. The mixture was ice-cooled, and then 22 g of p-nitrobenzyloxycarbonyl chloride were added. 14 ml of triethylamine were then added dropwise to the resulting mixture and the whole mixture was stirred for 1 hour, with ice-cooling. At the end of this time, water was added and the mixture was then extracted with methylene chloride, washed with water and dried. The solvent was distilled off under reduced pressure and the residue was purified by column chromatography through silica gel, eluted with a 1:1 by volume mixture of benzene and ethyl acetate, to give the title compound.

Nuclear Magnetic Resonance Spectrum (heptadeuterated dimethyl formamide ) δppm: 1.6–2.1 (2H, multiplet); 2.3 (3H, singlet); 3.2–3.7 (4H, multiplet); 4.2–4.5 (1H, multiplet); 5.2 (2H, singlet); 7.7, 8.2 (4H, $A_2B_2$, J=9.0 Hz).

PREPARATION 2

3-Methanesulphonyloxy-1-(N-p-nitrobenzyloxycarbonylacetimidoyl)pyrrolidine

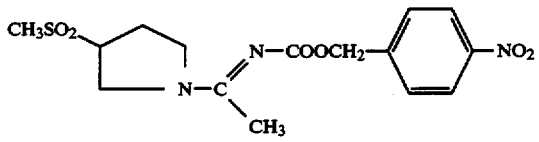

To a solution of 32.2 g of 3-hydroxy-1-(N-p-nitrobenzyloxycarbonylacetimidoyl)pyrrolidine in 500 ml of methylene chloride, were added, with ice-cooling, 9.3 ml of methanesulphonyl chloride, followed by 16.7 ml of triethylamine. The mixture was stirred for 30 minutes, with ice-cooling, and then water was added, after which the mixture was extracted with methylene chloride and the extract was washed with water and dried, to give 36 g of the title compound.

Nuclear Magnetic Resonance Spectrum ($CDCl_3$) δppm: 2.3 (3H, singlet); 2.0–2.6 (2H, multiplet); 3.1 (3H, singlet); 3.3–3.9 (4H, multiplet); 5.2 ([2] *2H*, singlet); 7.55, 8.20 (4H, $A_2B_2$, J=9.0 Hz).

PREPARATION 3

3-Acetylthio-1-(N-p-nitrobenzyloxycarbonylacetimidoyl)pyrrolidine

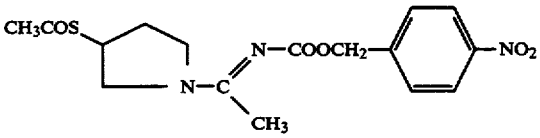

To 300 ml of anhydrous N,N-dimethylformamide were added 7.35 g of sodium hydride in the form of a 55% w/w/ dispersion in oil, followed by 12.5 g of thioacetic acid. The mixture was then stirred for 10 minutes, with ice-cooling, after which 40 g of 3-methanesulphonyloxy-1-(N-p-nitrobenzyloxycarbonylacetimidoyl)pyrrolidine were added. The mixture was then stirred for 3 hours at 65° C. After the reaction mixture had been allowed to cool, water was added and the mixture was extracted with ethyl acetate. The extract was washed with water and dried and then the solvent was distilled off under reduced pressure. The residue was purified by chromatography through a column of silica gel, eluted with a 2:1 by volume mixture of benzene and ethyl acetate, to give 30 g of the title compound.

Nuclear Magnetic Resonance Spectrum ($CDCl_3$) δppm: 1.8–2.2 (2H, multiplet); 2.25 (3H, singlet); 2.35 (3H, singlet); 3.2–4.2 (5H, multiplet); 5.2 (2H, singlet); 7.5, 8.2 (4H, $A_2B_2$, J=8.0 Hz).

PREPARATION 4

3-Mercapto-1-(N-p-nitrobenzyloxycarbonylacetimidoyl)pyrrolidine

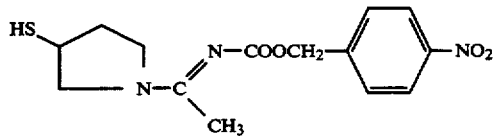

A solution of 30 g of 3-acetylthio-1-(N-p-nitrobenzyloxycarbonylacetimidoyl)pyrrolidine in 1000 ml of methanol was cooled to −10° C. A solution of sodium methoxide in methanol (prepared from 1.8 g of sodium) was then added dropwise to the cooled solution, after which the mixture was stirred for 30 minutes, whilst gradually raising the temperature to 0° C. At the end of this time, 65.2 ml of 10% w/v hydrochloric acid were added to the reaction mixture, which was then concentrated to half of its original volume by evaporation in vacuo. A saturated aqueous solution of sodium chloride was added to the concentrate and the mixture was extracted with ethyl acetate. The extract was washed with a saturated aqueous solution of sodium chloride and then dried, after which the solvent was distilled off under reduced pressure. The residue was purified by chromatography through a column of silica gel, eluted with a 2:1 by volume mixture of benzene and ethyl acetate, to give 20 g of the title compound.

Nuclear Magnetic Resonance Spectrum ($CDCl_3$) δppm: 1.7–2.7 (3H, multiplet); 2.3 (3H, singlet); 3.2–4.1 (5H, multiplet); 5.2 (2H, singlet); 7.5, 8.2 (4H, $A_2B_2$, J=8.0 Hz).

We claim:

1. Compounds of the formula (I):

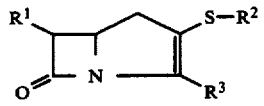

(I)

wherein $R^1$ is hydroxyethyl, $R^2$ is

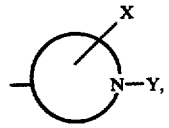

wherein

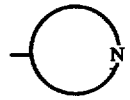

is a 3-pyrrolidinyl group, X is hydrogen and Y is [a group of the formula] *an acetimidoyl group,*

$-\underset{\underset{R^5}{|}}{C}=H-R^6$, ]

[wherein $R^5$ and $R^6$ are the same or different and each is hydrogen or an alkyl group having from 1 to 4 carbon atoms,]

$R^3$ is a carboxy group or a protected carboxy group; and pharmaceutically acceptable salts thereof.

2. The [compounds of claim 1, wherein Y is an acetimidoyl group] *compound of claim 1 which is (5R,6S)-2-(1-acetimidoylpyrrolidin-3-ylthio)-6-[1-(R)-hydroxyethyl]-2-carbapenem-3-carboxylic acid.*

3. The compounds of claim 1, wherein $R^3$ is a carboxy group.

4. The compounds of claim 1 in the form of the sodium [or potassium] salt.

5. The compounds of claim [2] *1* in the form of the [sodium or] potassium salt.

6. The compound of claim 1 which is 2-(1-acetimidoylpyrrolidin-3-ylthio)-6-(1-hydroxyethyl)-2-carbapenem-3-carboxylic acid.

[7. The compound of claim 1 which is 2-(1-formimidoylpyrrolidin-3-ylthio)-6-(1-hydroxyethyl)-2-carbapenem-3-carboxylic acid.]

8. A pharmaceutical composition comprising an effective amount of an antibacterial agent in admixture with a pharmaceutically acceptable carrier or diluent, wherein the antibacterial agent is selected from compounds of the formula (I):

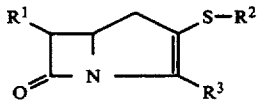

(I)

wherein $R^1$ is hydroxyethyl, $R^2$ is

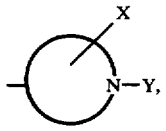

wherein

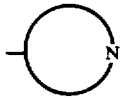

is a 3-pyrrolidinyl group, X is hydrogen and Y is [a] *an acetimidoyl group,* group of the formula $-\underset{\underset{R^5}{|}}{C}=H-R^6$, ]

[wherein $R^5$ and $R^6$ are the same or different and each is hydrogen or an alkyl group having from 1 to 4 carbon atoms,]

$R^3$ is a carboxy group or a protected carboxy group; and pharmaceutically acceptable salts thereof.

9. The composition of claim 8, wherein in said formula Y is an acetimidoyl group] *said antibacterial agent is (5R,6S)-2-(1-acetimidoylpyrrolidin-3-ylthio)-6-[1-(R)-hydroxyethyl]-2-carbapenem-3-carboxylic acid.*

10. The composition of claim 8, wherein $R^3$ is a carboxy group.

11. The composition of claim 8, wherein said compound is in the form of the sodium [or potassium] salt.

12. The composition of claim [9] *8,* wherein said compound is in the form of the [sodium or] potassium salt.

13. The composition of claim 8, wherein said antibacterial agent is 2-(1-acetimidoylpyrrolidin-3-ylthio)-6-(1-hydroxyethyl)-2-carbapenem-3-carboxylic acid.

[14. The composition of claim 8, wherein said antibacterial agent is 2-(1-formimidoylpyrrolidin-3-ylthio)-6-(1-hydroxyethyl)-2-carbapenem-3-carboxylic acid.]

* * * * *